US007816507B2

(12) United States Patent
Tian et al.

(10) Patent No.: US 7,816,507 B2
(45) Date of Patent: Oct. 19, 2010

(54) METHODS AND COMPOSITIONS FOR MODIFYING PLANT BIOSYNTHETIC PATHWAYS

(75) Inventors: Li Tian, Denton, TX (US); Richard A. Dixon, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 665 days.

(21) Appl. No.: 11/672,832

(22) Filed: Feb. 8, 2007

(65) Prior Publication Data

US 2008/0282423 A1 Nov. 13, 2008

Related U.S. Application Data

(60) Provisional application No. 60/772,354, filed on Feb. 9, 2006.

(51) Int. Cl.
*C12N 15/29* (2006.01)
*C12N 15/52* (2006.01)
*C12N 15/82* (2006.01)
*A01H 5/00* (2006.01)
*A01H 5/10* (2006.01)

(52) U.S. Cl. .................... 536/23.6; 536/23.4; 536/23.2; 536/23.1; 435/320.1; 435/182; 800/260; 800/287; 800/298

(58) Field of Classification Search ........................ None
See application file for complete search history.

(56) References Cited

U.S. PATENT DOCUMENTS

| 5,545,818 A | 8/1996 | McBride et al. | ............. | 800/279 |
| 2004/0093632 A1 | 5/2004 | Dixon et al. | ................. | 800/278 |
| 2006/0123508 A1 | 6/2006 | Dixon et al. | ................. | 800/278 |

FOREIGN PATENT DOCUMENTS

| WO | WO 00/04175 | 1/2000 |
| WO | WO 00/44909 | 8/2000 |
| WO | WO 02/066625 | 8/2002 |
| WO | WO 03/031622 | 4/2003 |
| WO | WO 03/040306 | 5/2003 |
| WO | WO 03/093464 | 11/2003 |
| WO | WO 2004/024079 | 3/2004 |
| WO | WO 2004/090136 | 10/2004 |

OTHER PUBLICATIONS

Akashi T. et al. Plant Physiology, Mar. 25, 2005; vol. 137, pp. 882-891.*
Lapcik, O. Phytochemistry 2007, vol. 68, pp. 2909-2916.*
Batard et al., "Molecular cloning and functional expression in yeast of CYP76B1, a xenobiotic-inducible 7-ethoxycoumarin O-deethylase from helianthus tuberosus," *The Plant Journal*, 14(1):111-120, 1998.

Didierjean et al., "Engineering herbicide metabolism in tobacco and arabidopsis with CYP76B1, a cytochrome P450 enzyme from jerusalem artichoke," *Plant Physiology*, 130:179-189, 2002.
Liu et al., "Metabolic engineering of isoflavonoid biosynthesis in arabidopsis thaliana," *Plant Biology*, Abstracts of the Annual Meeting of the American Society of Plant Physiologists, Abst. #269, p. 1, 2000.
Muir et al., "Overexpression of petunia chalcone isomerase in tomato results in fruit containing increased levels of flavonols," *Nature Biotechnology*, 19:470-474, 2001.
Shiota et al., "Expression of human cytochromes P450 1A1 and P450 1A2 as fused enzymes with yeast NADPH-cytochrome P450 oxidoreductase in transgenic tobacco plants," *Biosci. Biotechnol. Biochem.*, 64(10):2025-2033, 2000.
Shiota et al., "Herbicide-resistant tobacco plants expressing the fused enzyme between rat cytochrome P4501A 1 (CYP1A1) and yeast NADPH-cytochrome P450 oxidoreductase," *Plant Physiol.*, 106:17-23, 1994.
Winkel-Shirley, "Evidence for enzyme complexes in the phenylpropanoid and flavonoid pathways," *Physiol. Plant*, 107:142-149, 1999.
Yilmaz et al., "Enhanced stress tolerance in *Escherichia coli* and nicotiana tabacum expressing a betaine aldehyde dehydrogenase/ choline dehydrogenase fusion protein," *Biotechnol. Prog.*, 18:1176-1182, 2002.
Akashi et al., "Molecular and biochemical characterization of 2-hydroxyisoflavanone dehydratase. Involvement of carboxylesterase-like proteins in leguminous isoflavone biosynthesis," *Plant Physiol.*, 137:882-891, 2005.
Arai et al., "Design of the linkers which effectively separate domains of a bifunctional fusion protein," *Protein Eng.*, 14:529-532, 2001.
Barnes, "Soy isoflavones—phytoestrogens and what else?," *J. Nutr.*, 134:1225S-1228S, 2004.
Beaujean et al., "Engineering direct fructose production in processed potato tubers by expressing a bifunctional alpha-amylase/glucose isomerase gene complex," *Biotechnol. Bioeng.*, 70:9-16, 2000.
Bülow, "Preparation of artificial bifunctional enzymes by gene fusion," *Biochem. Soc. Symp.*, 57:123-133, 1990.
Cornwell et al., "Dietary phytoestrogens and health," *Phytochemistry*, 65:995-1016, 2004.
Deavours and Dixon, "Metabolic engineering of isoflavonoid biosynthesis in alfalfa," *Plant Physiol.*, 138:2245-2259, 2005.
DellaPenna, "Nutritional Genomics: Manipulating Plant Micronutrients to Improve Human Health," *Science*, 285:375-379, 1999.
Dixon and Ferreira, "Genistein," *Phytochemistry*, 60:205-211, 2002.
Dixon, "Engineering of plant natural product pathways," *Curr. Opin. Plant Biol.*, 8:329-336, 2005.
Dixon, "Natural products and plant disease resistance," *Nature*, 411:843-847, 2001.

(Continued)

*Primary Examiner*—Russell Kallis
(74) *Attorney, Agent, or Firm*—Steven P. Rhines, Esq.; Sonnenschein Nath & Rosenthal LLP

(57) ABSTRACT

The invention provides bifunctional plant biosynthetic enzymes that increase the efficiency by which modification can be made to plant biosynthetic pathways. In certain aspects of the invention, bifunctional isoflavone biosynthetic enzymes are provided. The invention therefore allows the modification of plants for isoflavone content. The inventors have demonstrated increased isoflavone biosynthesis can be obtained even in non-legume plants.

23 Claims, 13 Drawing Sheets

OTHER PUBLICATIONS

Dixon, "Phytoestrogens," *Annu. Rev. Plant Biol.*, 55:225-261, 2004.
Galili and Hofgen, "Metabolic engineering of amino acids and storage proteins in plants," *Metab. Eng.*, 4:3-11, 2002.
Gowri et al., "Stress Responses in Alfalfa (*Medicago sativa* L.): X. Molecular Cloning and Expression of S-Adenosyl-l-Methionine:Caffeic Acid 3-O-Methyltransferase, a Key Enzyme of Lignin Biosynthesis," *Plant Physiol.*, 97:7-14, 1991.
Hey et al., "Artificial, non-antibody binding proteins for pharmaceutical and industrial applications," *Trends Biotech.*, 23(10):514-522, 2005.
Hoffmann et al., "Purification, cloning, and properties of an acyltransferase controlling shikimate and quinate ester intermediates in phenylpropanoid metabolism," *J. Biol. Chem.*, 278:95-103, 2003.
James and Viola, "Production and Characterization of Bifunctional Enzymes. Substrate Channeling in the Aspartate Pathway," *Biochemistry*, 41:3726-3731, 2002.
Jang et al., "Expression of a bifunctional fusion of the *Escherichia coli* genes for trehalose-6-phosphate synthase and trehalose-6-phosphate phosphatase in transgenic rice plants increases trehalose accumulation and abiotic stress tolerance without stunting growth," *Plant Physiol.*, 131:516-524, 2003.
Jez et al., "Structure and mechanism of the evolutionarily unique plant enzyme chalcone isomerase," *Nat. Struct. Biol.*, 7:786-791, 2000.
Keung and Vallee, "Daidzin: a potent, selective inhibitor of human mitochondrial aldehyde dehydrogenase," *Proc. Natl Acad. Sci. USA*, 90:1247-1251, 1993.
Kim et al., "Construction and evaluation of a novel bifunctional N-carbamylase-D-hydantoinase fusion enzyme," *Appl. Environ. Microbiol.*, 66:2133-2138, 2000.
Kourtz et al., "A novel thiolase-reductase gene fusion promotes the production of polyhydroxybutyrate in Arabidopsis," *Plant Biotech J.*, 3:435-447, 2005.
La Camera et al., "Metabolic reprogramming in plant innate immunity: the contributions of phenylpropanoid and oxylipin pathways," *Immunol. Rev.*, 198:267-284, 2004.
Li et al., "A novel bifunctional fusion enzyme catalyzing ethylene synthesis via 1-aminocyclopropane1-carboxylic acid," *J. Biol. Chem.*, 271:25738-25741, 1996.
Liu et al., "Bottlenecks for metabolic engineering of isoflavone glycoconjugates in Arabidopsis," *Proc. Natl. Acad Sci. USA*, 99:14578-14583, 2002.
Liu et al., "Regiospecific hydroxylation of isoflavones by cytochrome p450 81E enzymes from *Medicago truncatula*," *Plant J.*, 36:471-484, 2003.
Netzer and Hartl, "Recombination of protein domains facilitated by co-translational folding in eukaryotes," *Nature*, 388:343-349, 1997.
Nixon et al., "Hybrid enzymes: manipulating enzyme design," *Trends Biotechnol.*, 16:258-264, 1998.
Paiva et al., "Stress responses in alfalfa (*Medicago sativa* L.) 11. Molecular cloning and expression of alfalfa isoflavone reductase, a key enzyme of isoflavonoid phytoalexin biosynthesis," *Plant Mol. Biol.*, 17:653-667, 1991.
Reddy et al., "Targeted down-regulation of cytochrome P450 enzymes for forage quality improvement in alfalfa (*Medicago sativa* L.)," *Proc. Natl. Acad. Sci. USA*, 102:16573-16578, 2005.
Sawada et al., "Key amino acid residues required for aryl migration catalysed by the cytochrome P450 2-hydroxyisoflavanone synthase," *Plant J.*, 31:555-564, 2002.
Schoch et al., "CYP98A3 from *Arabidopsis thaliana* is a 3'-hydroxylase of phenolic esters, a missing link in the phenylpropanoid pathway," *J. Biol. Chem.*, 276:36566-36574, 2001.
Seo et al., "Characterization of a bifunctional enzyme fusion of trehalose-6-phosphate synthetase and trehalose-6-phosphate phosphatase of *Escherichia coli*," *Appl. Environ. Microbio.*, 66:2484-2490, 2000.
Shimada et al., "A cluster of genes encodes the two types of chalcone isomerase involved in the biosynthesis of general flavonoids and legume-specific 5-deoxy(iso)flavonoids in *Lotus japonicus*," *Plant Physiol.*, 131:941-951, 2003.
Skerra, "Imitating the humoral immune response," *Curr. Opin. Chem. Biol.*, 7:683-693, 2003.
Tattersall et al., "Resistance to an Herbivore Through Engineered Cyanogenic Glucoside Synthesis," *Science*, 293:1826-1828, 2001.
Thelen and Ohlrogge, "Metabolic engineering of fatty acid biosynthesis in plants," *Metab. Eng.*, 4:12-21, 2002.
Tian and Dixon, "Engineering isoflavone metabolism with an artificial bifunctional enzyme," *Planta*, 224:496-507, 2006.
Williams et al., "Mammalian microsomal cytochrome P450 monooxygenase: structural adaptations for membrane binding and functional diversity," *Mol. Cell*, 5:121-131, 2000.
Ralston et al., "Partial Reconstruction of Flavonoid and Isoflavonoid Biosynthesis in Yeast Using Soybean Type I and Type II Chalcone Isomerases," *Plant Physiology*, 137:1375-1388, 2005.

\* cited by examiner (a)

SEQUENCE LISTING

```
<160> NUMBER OF SEQ ID NOS: 38

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
atggtaccat gttgcttgaa cttgca                                              26
```

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic Primer

<400> SEQUENCE: 2
taggatccag aaaggagttt agatgca    27

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic Primer

<400> SEQUENCE: 3
atggatccgg aatggctgca tcaatc    26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic Primer

<400> SEQUENCE: 4
tagagctctc agtttccaat cttgaa    26

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic Primer

<400> SEQUENCE: 5
tagagctctt aagaaaggag tttag    25

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic Primer

<400> SEQUENCE: 6
atggtaccat ggctgcatca atc    23

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic Primer

<400> SEQUENCE: 7
attctagaat gttgcttgaa cttgca    26

```
<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
attctagaat ggctgcatca atc                                              23

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
atctcgagat gttgcttgaa cttgca                                           26

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gcccttgctc accatgtttc caatcttgaa                                       30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
ttcaagattg gaaacatggt gagcaagggc                                       30

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
agttatctag agtcgcggcc                                                  20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
atctcgagat ggtgagcaag ggc                                              23
```

```
<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
gatatggaaa agatctggca tcac                                          24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
tcatactcgg ccttggagat ccac                                          24

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
gctgcatcaa tcaccgcaat ca                                            22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
gtttccaatc ttgaaagcac                                               20

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
ggctacttcg ggaatggcaa cac                                           23

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
taaaagtcaa gggtctcaag taac                                          24
```

<210> SEQ ID NO 20
<211> LENGTH: 2241
<212> TYPE: DNA
<213> ORGANISM: Artificial Sequence
<220> FEATURE:
<223> OTHER INFORMATION: Description of Artificial Sequence: Synthetic Primer

<400> SEQUENCE: 20

| | | | | | |
|---|---|---|---|---|---|
| atgttgcttg | aacttgcact | tggtttattg | gttttggctc | tgtttctgca | cttgcgtccc | 60 |
| acacccactg | caaaatcaaa | agcacttcgc | catctcccaa | acccaccaag | cccaaagcct | 120 |
| cgtcttccct | tcataggaca | ccttcatctc | ttaaaagaca | aacttctcca | ctacgcactc | 180 |
| atcgacctct | ccaaaaaaca | tggtcccttg | ttctctctct | actttggctc | catgccaacc | 240 |
| gttgttgcct | ccacaccaga | attgttcaag | ctcttcctcc | aaacgcacga | ggcaacttcc | 300 |
| ttcaacacaa | ggttccaaac | ctcagccata | agacgcctca | cctatgatag | ctcagtggcc | 360 |
| atggttccct | tcggacctta | ctggaagttc | gtgaggaagc | tcatcatgaa | cgaccttctc | 420 |
| aacgccacca | ctgtaaacaa | gttgaggcct | tgaggaccc | aacagatccg | caagttcctt | 480 |
| agggttatgg | cccaaggcgc | agaggcacag | aagccccttg | acttgaccga | ggagcttctg | 540 |
| aaatggacca | acagcaccat | ctccatgatg | atgctcggcg | aggctgagga | gatcagagac | 600 |
| atcgctcgcg | aggttcttaa | gatctttggc | gaatacagcc | tcactgactt | catctggcca | 660 |
| ttgaagcatc | tcaaggttgg | aaagtatgag | aagaggatcg | acgacatctt | gaacaagttc | 720 |
| gaccctgtcg | ttgaaagggt | catcaagaag | cgccgtgaga | tcgtgaggag | agaaagaac | 780 |
| ggagaggttg | ttgagggtga | ggtcagcggg | gttttccttg | acactttgct | tgaattcgct | 840 |
| gaggatgaga | ccatggagat | caaaatcacc | aaggaccaca | tcaagggtct | tgttgtcgac | 900 |
| ttttctcgg | caggaacaga | ctccacagcg | gtggcaacag | agtgggcatt | ggcagaactc | 960 |
| atcaacaatc | ctaaggtgtt | ggaaaaggct | cgtgaggagg | tctacagtgt | tgtgggaaag | 1020 |
| gacagacttg | tggacgaagt | tgacactcaa | aaccttcctt | acattagagc | aatcgtgaag | 1080 |
| gagacattcc | gcatgcaccc | gccactccca | gtggtcaaaa | gaaagtgcac | agaagagtgt | 1140 |
| gagattaatg | gatatgtgat | cccagaggga | gcattgattc | tcttcaatgt | atggcaagta | 1200 |
| ggaagagacc | ccaaatactg | gacagacca | tcggagttcc | gtcctgagag | gttcctagag | 1260 |
| acagggctg | aagggggaagc | agggcctctt | gatcttaggg | gacaacattt | tcaacttctc | 1320 |
| ccatttgggt | ctgggaggag | aatgtgccct | ggagtcaatc | tggctacttc | gggaatggca | 1380 |
| acacttcttg | catctcttat | tcagtgcttc | gacttgcaag | tgctgggtcc | acaaggacag | 1440 |
| atattgaagg | gtggtgacgc | caaagttagc | atggaagaga | gagccggcct | cactgttcca | 1500 |
| agggcacata | gtcttgtctg | tgttccactt | gcaaggatcg | gcgttgcatc | taaactcctt | 1560 |
| tctggatccg | gaatggctgc | atcaatcacc | gcaatcactg | tggagaacct | tgaatacca | 1620 |
| gcggtggtta | cctctccggt | caccggcaaa | tcatatttcc | tcggtggcgc | tggggagaga | 1680 |
| ggattgacca | ttgaaggaaa | cttcatcaag | ttcactgcca | taggtgttta | tttggaagat | 1740 |
| atagcagtg | cttcactagc | tgccaaatgg | aagggtaaat | catctgaaga | gttacttgag | 1800 |
| acccttgact | tttacagaga | catcatctca | ggtcccttg | aaaagttaat | tagagggtca | 1860 |
| aagattaggg | aattgagtgg | tcctgagtac | tcaaggaagg | ttatggagaa | ctgtgtggca | 1920 |
| cacttgaaat | cagttggaac | ttatggagat | gcagaagctg | aagctatgca | aaaatttgct | 1980 |
| gaagctttca | agcctgttaa | ttttccacct | ggtgcctctg | ttttctacag | gcaatcacct | 2040 |
| gatggaatat | tagggcttag | tttctctccg | gatacaagta | taccagaaaa | ggaggctgca | 2100 |

```
ctcatagaga acaaggcagt ttcatcagca gtgttggaga ctatgatcgg cgagcacgct    2160
gtttcccctg atcttaagcg ctgtttagct gcaagattac ctgcgttgtt gaacgagggt    2220
gctttcaaga ttggaaactg a                                              2241

<210> SEQ ID NO 21
<211> LENGTH: 669
<212> TYPE: DNA
<213> ORGANISM: Medicago sativa

<400> SEQUENCE: 21
atggctgcat caatcaccgc aatcactgtg gagaaccttg aatacccagc ggtggttacc      60
tctccggtca ccggcaaatc atatttcctc ggtggcgctg gggagagagg attgaccatt     120
gaaggaaact tcatcaagtt cactgccata ggtgtttatt ggaagatat agcagtggct      180 tcactagctg ccaaatggaa gggtaaatca tctgaagagt tacttgagac ccttgacttt     240
tacagagaca tcatctcagg tccctttgaa aagttaatta gagggtcaaa gattagggaa     300
ttgagtggtc ctgagtactc aaggaaggtt atggagaact gtgtggcaca cttgaaatca     360
gttgaacttt atggagatgc agaagctgaa gctatgcaaa aatttgctga agctttcaag     420
cctgttaatt ttccacctgg tgcctctgtt ttctacaggc aatcacctga tggaatatta     480
gggcttagtt tctctccgga tacaagtata ccagaaaagg aggctgcact catagagaac     540
aaggcagttt catcagcagt gttggagact atgatcggcg agcacgctgt tcccctgat      600 cttaagcgct gtttagctgc aagattacct gcgttgttga cgagggtgc tttcaagatt      660 ggaaactga                                                            669

<210> SEQ ID NO 22
<211> LENGTH: 1566
<212> TYPE: DNA
<213> ORGANISM: Glycine max

<400> SEQUENCE: 22
atgttgcttg aacttgcact tggtttattg gttttggctc tgtttctgca cttgcgtccc      60
acacccactg caaaatcaaa agcacttcgc catctcccaa acccaccaag cccaaagcct     120
cgtcttccct tcataggaca ccttcatctc ttaaaagaca aacttctcca ctacgcactc     180
atcgacctct ccaaaaaaca tggtcccta ttctctctct actttggctc catgccaacc      240
gttgttgcct ccacaccaga attgttcaag ctcttcctcc aaacgcacga ggcaacttcc     300
ttcaacacaa ggttccaaac ctcagccata agacgcctca cctatgatag ctcagtggcc     360
atggttccct tcggacccta ctggaagttc gtgaggaagc tcatcatgaa cgaccttctc     420
aacgccacca ctgtaaacaa gttgaggcct tgaggaccc aacagatccg caagttcctt     480
agggttatgg cccaaggcgc agaggcacag aagcccttg acttgaccga ggagcttctg     540
aaatggacca acagcaccat ctccatgatg atgctcggcg aggctgagga gatcagagac     600
atcgctcgcg aggttcttaa gatctttggc gaatacagcc tcactgactt catctggcca     660
ttgaagcatc tcaaggttgg aaagtatgag aagaggatcg acgacatctt gaacaagttc     720
gaccctgtcg ttgaaagggt catcaagaag cgccgtgaga tcgtgaggag gagaaagaac     780
ggagaggttt tgagggtga ggtcagcggg gttttccttg acacttttgct tgaattcgct     840 gaggatgaga ccatggagat caaaatcacc aaggaccaca tcaagggtct tgttgtcgac     900 ttttctcgg caggaacaga ctccacagcg gtggcaacag agtgggcatt ggcagaactc     960
atcaacaatc ctaaggtgtt ggaaaaggct cgtgaggagg tctacagtgt tgtgggaaag    1020
```

-continued

```
gacagacttg tggacgaagt tgacactcaa aaccttcctt acattagagc aatcgtgaag    1080
gagacattcc gcatgcaccc gccactccca gtggtcaaaa gaaagtgcac agaagagtgt    1140
gagattaatg gatatgtgat cccagaggga gcattgattc tcttcaatgt atggcaagta    1200
ggaagagacc ccaaatactg ggacagacca tcggagttcc gtcctgagag gttcctagag    1260 acagggctg aaggggaagc agggcctctt gatcttaggg gacaacattt tcaacttctc     1320
ccatttgggt ctgggaggag aatgtgccct ggagtcaatc tggctacttc gggaatggca    1380
acacttcttg catctcttat tcagtgcttc gacttgcaag tgctgggtcc acaaggacag    1440
atattgaagg gtggtgacgc caaagttagc atggaagaga gagccggcct cactgttcca    1500
agggcacata gtcttgtctg tgttccactt gcaaggatcg gcgttgcatc taaactcctt    1560
tcttaa                                                              1566
```

<210> SEQ ID NO 23
<211> LENGTH: 720
<212> TYPE: DNA
<213> ORGANISM: C. ELEGANS

<400> SEQUENCE: 23

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 24
<211> LENGTH: 2958
<212> TYPE: DNA
<213> ORGANISM: Artificial Sequence
<220> FEATURE:
<223> OTHER INFORMATION: Description of Artificial Sequence: Synthetic Primer

<400> SEQUENCE: 24

```
atgttgcttg aacttgcact tggtttattg gttttggctc tgtttctgca cttgcgtccc     60
acacccactg caaaatcaaa agcacttcgc catctcccaa acccaccaag cccaaagcct    120
cgtcttccct tcataggaca ccttcatctc ttaaaagaca aacttctcca ctacgcactc    180
atcgacctct ccaaaaaaca tggtcccttat ttctctctct actttggctc catgccaacc    240
gttgttgcct ccacaccaga attgttcaag ctcttcctcc aaacgcacga ggcaacttcc    300
ttcaacacaa ggttccaaac ctcagccata agacgcctca cctatgatag ctcagtggcc    360
atggttccct tcggacctta ctggaagttc gtgaggaagc tcatcatgaa cgaccttctc    420
aacgccacca ctgtaaacaa gttgaggcct ttgaggaccc aacagatccg caagttcctt    480
```

```
agggttatgg cccaaggcgc agaggcacag aagcccttg acttgaccga ggagcttctg    540
aaatggacca acagcaccat ctccatgatg atgctcggcg aggctgagga gatcagagac    600
atcgctcgcg aggttcttaa gatctttggc gaatacagcc tcactgactt catctggcca    660
ttgaagcatc tcaaggttgg aaagtatgag aagaggatcg acgacatctt gaacaagttc    720
gaccctgtcg ttgaaagggt catcaagaag cgccgtgaga tcgtgaggag gagaaagaac    780
ggagaggttg ttgagggtga ggtcagcggg gttttccttg acactttgct tgaattcgct    840
gaggatgaga ccatggagat caaaatcacc aaggaccaca tcaagggtct tgttgtcgac    900
tttttctcgg caggaacaga ctccacagcg gtggcaacag agtgggcatt ggcagaactc    960
atcaacaatc ctaaggtgtt ggaaaaggct cgtgaggagg tctacagtgt tgtgggaaag    1020
gacagacttg tggacgaagt tgacactcaa aaccttcctt acattagagc aatcgtgaag    1080
gagacattcc gcatgcaccc gccactccca gtggtcaaaa gaaagtgcac agaagagtgt    1140
gagattaatg gatatgtgat cccagaggga gcattgattc tcttcaatgt atggcaagta    1200
ggaagagacc ccaaatactg ggacagacca tcggagttcc gtcctgagag gttcctagag    1260
acaggggctg aaggggaagc agggcctctt gatcttaggg gacaacattt tcaacttctc    1320
ccatttgggt ctgggaggag aatgtgccct ggagtcaatc tggctacttc gggaatggca    1380
acacttcttg catctcttat tcagtgcttc gacttgcaag tgctgggtcc acaaggacag    1440
atattgaagg gtggtgacgc caaagttagc atggaagaga gagccggcct cactgttcca    1500
agggcacata gtcttgtctg tgttccactt gcaaggatcg gcgttgcatc taaactcctt    1560
tctggatccg gaatggctgc atcaatcacc gcaatcactg tggagaacct tgaatacca    1620 gcggtggtta cctctccggt caccggcaaa tcatatttcc tcggtggcgc tggggagaga    1680
ggattgacca ttgaaggaaa cttcatcaag ttcactgcca taggtgttta tttggaagat    1740
atagcagtgg cttcactagc tgccaaatgg aagggtaaat catctgaaga gttacttgag    1800
acccttgact tttacagaga catcatctca ggtcccttg aaaagttaat tagagggtca    1860
aagattaggg aattgagtgg tcctgagtac tcaaggaagg ttatggagaa ctgtgtggca    1920
cacttgaaat cagttggaac ttatggagat gcagaagctg aagctatgca aaaatttgct    1980
gaagctttca gcctgttaa ttttccacct ggtgcctctg ttttctacag gcaatcacct    2040
gatggaatat tagggcttag tttctctccg gatacaagta taccagaaaa ggaggctgca    2100
ctcatagaga acaaggcagt tcatcagca gtgttggaga ctatgatcgg cgagcacgct    2160 gtttccctg atcttaagcg ctgtttagct gcaagattac ctgcgttgtt gaacgagggt    2220
gctttcaaga ttggaaacat ggtgagcaag ggcgaggagc tgttcaccgg ggtggtgccc    2280
atcctggtcg agctggacgg cgacgtaaac ggccacaagt tcagcgtgtc cggcgagggc    2340
gagggcgatg ccacctacgg caagctgacc ctgaagttca tctgcaccac cggcaagctg    2400
cccgtgccct ggcccaccct cgtgaccacc ctgacctacg gcgtgcagtg cttcagccgc    2460
taccccgacc acatgaagca gcacgacttc ttcaagtccg ccatgcccga aggctacgtc    2520
caggagcgca ccatcttctt caaggacgac ggcaactaca agacccgcgc cgaggtgaag    2580
ttcgagggcg acaccctggt gaaccgcatc gagctgaagg gcatcgactt caaggaggac    2640
ggcaacatcc tggggcacaa gctggagtac aactacaaca gccacaacgt ctatatcatg    2700
gccgacaagc agaagaacgg catcaaggtg aacttcaaga tccgccacaa catcgaggac    2760
ggcagcgtgc agctcgccga ccactaccag cagaacaccc ccatcggcga cggccccgtg    2820
ctgctgcccg acaaccacta cctgagcacc cagtccgccc tgagcaaaga ccccaacgag    2880
```

```
aagcgcgatc acatggtcct gctggagttc gtgaccgccg ccgggatcac tctcggcatg    2940
gacgagctgt acaagtaa                                                   2958

<210> SEQ ID NO 25
<211> LENGTH: 2527
<212> TYPE: DNA
<213> ORGANISM: Nicotiana tabacum

<400> SEQUENCE: 25
caacattata cccatccctc tatttatacc acaattctta gcttcaataa ccaggatctt      60
tctacccatc ctcacattta attaataacc caattcttgt ttccaaaaat ataccttcaa     120
tttttcacta gacaaaccaa cccctttaca cttttactcc attttcttga atcatttcat     180
tttatttcat ctcacaaaaa aaaaatggct ggtgttgcac aaaatggtca ccaagaaatg     240 gattttgca tgaaagtgga tccattaaac tgggaaatgg cagctgattc attgaaagga      300
agccatttag atgaagtgaa gaaatggtg gctgagttta ggaaaccagt agtgaaactt      360
ggaggtgaga ctttgacagt ggctcaagtt gcggctattg ctgcaaaaga taatgttaaa     420
actgttaaag tggagctttc tgaagggca agagctggtg ttaaagctag cagtgattgg      480
gttatggaca gtatgggtaa aggaactgat agttatggtg ttacaactgg ctttggtgct     540
acttcacata ggaggaccaa gatggtggt gctcttcaaa aggaacttat taggttcttg      600
aatgctggag ttttggcaa tggaacagag tcatgtcaca cattaccaca atcagggaca     660
agggcagcta tgttagttag gatcaacact ctccttcaag ggtactctgg catcagattt     720
gaaatcttag aagcaatcac taaattgctt aaccacaatg ttactccatg tttgccccctt    780 cgcggcacca tcaccgcctc tggtgatctc gtcccccttgt cctacattgc cggtttactc    840
actggtcggc ctaattctaa agcagttgga cctaatggcg aaaccctcaa cgctgaagaa    900
gcgtttcgtg ttgctggagt taacggtgga ttttcgagt tgcagcctaa ggaaggcctt    960
gctcttgtga atggtactgc agttggttct ggtttggcct caatggttct ctttgatgct    1020
aatgttctcg cggtcttttc tgaagttctc tcagctattt ttgctgaggt aatgaatgga    1080
aagcccgagt tcactgacca cttgacacac aagttgaagc atcaccccgg acaaattgag    1140
gctgctgcta ttatggaaca catttttggat ggtagctctt atgtgaaggc ggctcagaag    1200
cttcacgaaa cggatcctct ccaaaaacca aagcaagatc gttatgctct tagaacgtcg    1260
ccccaatggc ttggccctca aattgaggtc atccgttctg caaccaagat gattgagagg    1320
gagattaatt cagtgaacga caacccttg atcgatgttt caagaaacaa ggcattacac    1380
ggtggcaact tccagggcac tccaattggt gtctctatgg acaatgctag attagccctt    1440
gcatcaatag ggaaattgat gtttgccaa ttctccgagc ttgtcaacga ttactacaac    1500
aacggattgc catctaatct gacagcagga aggaatccta gcttggacta tggtttcaag    1560
ggatctgaga ttgccatggc ttcatactgt tcagaacttc aattcttggc aaatccagtg    1620
actaaccacg tacaaagcgc cgagcaacac aaccaagatg tgaactcctt ggacttaatc    1680
tcagctagaa aaacagctga agccgtggac atcttaaagc taatgtcatc cacatatcta    1740
gttgcacttt gccaagcaat agacttgagg catttggaag aaaatctgag gaatgcagtc    1800
aagaacacgt gagccaagt cgcaaagaga actttaacaa tgggtaccaa tggagaactt    1860
catccatcaa gattctgtga aaaggacttg cttcgagtcg tggacaggga atacgtcttc    1920
gcctatgctg acgacgcctg cagcgctaac tacccactga tgcagaaact aaggcaagtc    1980
ctcgtcgacc acgccttgca aaatggcgaa aatgagaaga acgcaaacag ctcaatcttc    2040
```

| | |
|---|---|
| caaaagatac tagcttttga agacgagcta aaggccgtgt tgccaaaaga agtcgagagt | 2100 |
| gcaagagccg cgctggaaag tgggaaccct gcaattgcca acaggataaa agaatgcaga | 2160 |
| tcttatccac tttacaggtt tgttagagga gaacttggag ctgaattatt gacgggagaa | 2220 |
| aaagtcaggt caccaggtga agaatgtgac aaagtgttca cagcaatgtg caatggacaa | 2280 |
| attattgatt cattgttaga atgtctcaag gaatggaatg gtgcacctct tccaatctgt | 2340 |
| tagaagttgg ttctcaaaca acaggatctt tgttaatgtt tgtcaattac ctgttatttt | 2400 |
| tctatttta cttttctt tggggttga ttaaatgtaa actctcttga atatgttggt | 2460 |
| ttgtagttgt attagtctct tttccgtaca ataaatgaa aagtgacaat gtgcttatat | 2520 |
| gttcttg | 2527 |

<210> SEQ ID NO 26
<211> LENGTH: 1352
<212> TYPE: DNA
<213> ORGANISM: Camellia sinensis

<400> SEQUENCE: 26

| | |
|---|---|
| atggtgttca ctgtatacgg tgagcactgg aggaagatga ggaggatcat gacggttcct | 60 |
| tttttttacca acaaggtggt gcagcagtac aggttcgggt gggaggacga ggcgggtcgg | 120 |
| gtcgtggagg atgtgaagaa gaacccggaa gcgaagacca tgggatcgt gctgaggagg | 180 |
| cggttgcagc tgatgatgta caataacatg tacaggatta tgtttgattc gaggttcgag | 240 |
| agcgaggagg acccgttgtt cgtgaaattg aaggcgttga atggagagag gagtaggttg | 300 |
| gctcagagct ttgagtataa ctacggcgat tttattccga ttttgaggcc gttcttgaga | 360 |
| gggtacttga agatctgcaa agaagttaaa gagaggaggt tgcagctttt caaggactat | 420 |
| tttgtcgatg aaaggaagaa gttagccaag ccacgaagag ccatggacac agttactcta | 480 |
| aaatgtgcga ttgatcatat tttggatgct caacaaaagg gagagatcaa cgaggacaac | 540 |
| gttctttaca tcgtggagaa cattaacgtc gctgcaattg agacaacatt atggtcgata | 600 |
| gaatggggca tagcagaact tgtaaaccac cccaaatcc agaaaaagct tcggcacgaa | 660 |
| cttgacacca tgcttggcct tggagtccaa atcaccgagc cagacaccta caaactcccc | 720 |
| tacctccaag ctgtagtcaa agagaccctc cgcctccgga tggcaattcc cctcttagtc | 780 |
| ccccacatga acctccacga tgcaaagctc tctggctatg acatccctgc tgagagcaaa | 840 |
| atcttggtaa acgcgtggtg gcttgcaaac aaccccgaca actggaagaa cccagaagag | 900 |
| ttcaggcccg agaggttctt ggaagaggag gctaaggttg aggccaatgg caatgacttt | 960 |
| aggtaccttc cgtttggtgt cggaaggagg agttgccctg gaattatcct tgctctgcca | 1020 |
| attctcggca tcactttggg aaggttggtt cagaatttcg agctcttgcc tcctccggga | 1080 |
| caggccaaga ttgatactgc tgagaagggg gacagttca gcttgcatat tttgaagcac | 1140 |
| tcgaccattg ttctgaaacc aagatcgttc tgattttcat aaatttatgt ttttgtttta | 1200 |
| ttgtgttttg aagtgagtgg ggtgggggtt gagaaggaat tggggagatg ttgatctgtg | 1260 |
| tgtgattgta aatctctgtt gatgtgcaag gacaattcag aagtttgcaa ggagtatttt | 1320 |
| tctaaaaaaa aaaaaaaaa aaaaaaaaa aa | 1352 |

<210> SEQ ID NO 27
<211> LENGTH: 1904
<212> TYPE: DNA
<213> ORGANISM: Medicago sativa

```
<400> SEQUENCE: 27
ggcacgaggg ttgcaagcaa tcccttcaaa ccaaaaaaaa ctataggcac attcacaatc      60
atatagctgc ataaattaac acaaaaccat atggattcgc ttctaaaatt tccaatcatg     120
gtgaacttga aggaagaacc atttcttatg gcaatcatgg tcatcgtacc actaacactc     180 ttgtttgggtt taatgtcacg aatcctcaaa agaccaagat atccaccagg accaaaaggg     240
ttacctatta taggtaacat gctaatgatg accaattaa cccaccgtgg tctagccaac     300
ttagccaaaa aatatggagg catctttcac ctacgcatgg gattcctcca catggtagct     360
atttccgacg cggacgccgc acgacaagtt ctccaagttc aagacaacat cttttccaac     420
cggccagcaa ctgtggctat taaataccta acttacgacc gtgctgacat ggcgttcgct     480
cactacggtc ccttttggcg ccagatgcga aaactctgcg tgatgaagct tttcagccgc     540
aagcacgcag agtcttggca atctgttaga gacgaggttg actatgctgt ccgaactgtt     600
tcggacaaca taggcaaccc tgtgaatatc ggagaactgg tgttcaattt aactaaaaac     660
attatatatc gagcggcttt cgggtcgagc tcaagagaag acaagatga gtttattgga     720 atattgcaag agttttccaa attgtttgga gcttttaata tttccgactt tgtaccttgt     780
tttggagcta ttgaccctca agggcttaat gctaggcttg tgaaggctcg taaagatttg     840
gatagtttca tagacaaaat catagatgaa catgtggaga agaagaagag tgttgttgat     900
gaagaaacgg atatggtgga tgagttgctt gctttctata gtgaggaggc taaattgaat     960
aatgaatcag atgatttgca taattccatc aaacttacca aggataacat caaagccatc    1020
ataatggacg tgatgtttgg aggaacggaa acggtagcat cagcaatcga atgggttatg    1080
gcagagttaa tgaaaagccc agaagaccta aaaaaagttc aacaagaact agcagaagtt    1140
gtgggtctga gccgacaggt tgaagaaccc gatttcgaga aactaaccta tctaaaatgc    1200
gctcttaagg aaaccctacg ccttcaccca ccaattcctt tgcttcttca tgaaactgcg    1260
gaagaagcaa cggttaatgg ttatttcatt ccaaagcaag cgcgcgtgat gataaacgca    1320
tgggctattg aagagacgc aaattgttgg gacgaacccg agagttttaa accgtcgcgg    1380 ttttttgaaac caggtgtgcc cgatttttaaa gggagtaatt ttgagtttat tccgtttggg    1440
tcaggacgta gatcctgtcc cggtatgcag ttgggtttgt atgcgcttga tttggcagtg    1500
gctcatttac ttcattgctt tacttgggag ttgccggatg gaatgaaacc gagtgagatg    1560
gatatgagtg atgtatttgg actcactgca ccaagagcga gtcgactcat tgctattcct    1620
actaagcgtg tcttgtgtcc tttggattaa aaagaaaaag aggaagaaaa aaaaatggac    1680
cttgaatttt ctattttgag tttttttttt attgttattc tattaaacaa taaggataag    1740
tgttatgtga tgataaaata agacacgtaa caagaacgtg agagtgtaaa agaattggaa    1800
ttttcttcac ttttcttgat gtaagcttct attttcaaat attataatgt attatcctat    1860
cctataagaa acaattcctt gtataaaaaa aaaaaaaaaa aaaa                      1904

<210> SEQ ID NO 28
<211> LENGTH: 1317
<212> TYPE: DNA
<213> ORGANISM: Medicago sativa

<400> SEQUENCE: 28
aatctcacaa aaacctcatc aatcacaacc atgggttcaa caggtgaaac tcaaataaca      60
ccaacccaca tatcagatga agaagcaaac ctcttcgcca tgcaactagc aagtgcttca     120
gttcttccca tgattttgaa atcagctctt gaacttgatc tcttagaaat cattgctaaa     180
```

```
gctggacctg gtgctcaaat ttcacctatt gaaattgctt ctcagctacc aacaactaac    240
cctgatgcac cagttatgtt ggaccgaatg ttgcgtctct tggcttgtta cataatcctc    300
acatgttcag ttcgtactca acaagatgga aaggttcaga gactttatgg tttggctact    360
gttgctaagt atttggttaa gaatgaagat ggtgtatcca tttctgctct taatctcatg    420
aatcaggata aagtgctcat ggaaagctgg taccacctaa agatgcagt ccttgatggg     480 ggcattccat tcaacaaggc ttatggaatg acagcctttg aataccatgg aacagatcca    540
aggtttaaca aggttttcaa caaggggatg tctgatcact ctaccatcac aatgaagaaa    600
attcttgaga cctacacagg ttttgaaggc cttaaatctc ttgttgatgt aggtggtggt    660
actggagctg taattaacac gattgtctca aaatatccca ctataaaggg tataaatttt    720
gatttacccc atgtcattga agatgctcca tcttatccag gagttgagca tgttggtgga    780
gacatgtttg tcagtattcc aaaggctgat gctgttttta tgaagtggat ttgtcatgac    840
tggagtgatg agcactgctt gaaatttttg aagaactgct atgaggcact gccagacaat    900
ggaaaagtga ttgtggcaga atgcatactt ccagtggctc cagattcaag cctggccaca    960
aaaggtgtgg ttcacattga tgtgatcatg ttggctcata atcctggtgg aaagagagaa   1020
acacaaaaag agtttgagga tcttgccaaa ggtgctggat tccaaggttt caaagtccat   1080
tgtaatgctt tcaacacata catcatggag tttcttaaga aggttaattt ctcttggtgt   1140
gttgcatctg agttttgata ttgagattgt ggttgtgctt ctacttacct aagctttccc   1200
cataaaaata tgtgatttcc acttctattc ggtaggaaaa taataatgag aaagttcatt   1260
gtaatattgc ctatataaat gaacattgtt tcatattgtg gattataaaa aaaaaaa     1317

<210> SEQ ID NO 29
<211> LENGTH: 1885
<212> TYPE: DNA
<213> ORGANISM: Arabidopsis thaliana

<400> SEQUENCE: 29
atcaaagtct ccaccacata tatctagaag aattctacaa gtgaattcga tttacacttt     60 ttttttgtcct tttttattaa taaatcactg acccgaaaat aaaaatagaa gcaaaacttc    120
atgtcgtggt ttctaatagc ggtggcgaca atcgccgccg tcgtatccta caagctaatc    180
caacggctaa gatacaagtt cccaccaggc ccaagcccca agccgatcgt cggtaaccct    240
tacgacataa aaccggtccg gttcagatgt tactacgagt gggctcaatc ttatggacca    300
atcatatcgg tctggatcgg ttcaattcta aacgtggtcg tatctagcgc cgagctagca    360
aaagaagttc tgaaagaaca cgaccagaaa ctcgccgacc ggcaccggaa cagatcgacg    420
gaagcattta gccgcaacgg tcaggatctt atatgggccg attatgggcc tcattacgtg    480
aaggtgagaa aagtttgcac gcttgagctc ttcacaccga aacgactcga gtctctcaga    540
cctatccgtg aagatgaagt caccgccatg ttgaatccgc tcttcagaga ctgtaacctt    600
cctgaaaaca gagcaaaagg tttacaactg aggaagtact taggagcggt tgcgttcaac    660
aacataacgc ggctagcctt tgggaagcgt tttatgaacg ctgaaggtgt tgtggacgag    720
caagggcttg agttcaaggc catagtatcc aacggtctga agctaggtgc ttcactgtca    780
atagctgaac acatcccgtg gctcaggtgg atgtttccgg ctgatgagaa ggcgtttgct    840
gagcacgggg ctcgtcgtga ccgcctcact cgagctatca tggaggagca tacttttggcc    900 cgtcaaaagt ctagtggagc gaaacagcat ttcgttgatg cgttgctaac gttgaaggat    960
cagtatgatc ttagtgagga tactatcatt ggtcttctat gggatatgat cacggcaggg   1020
```

```
atggacacga cagcgataac agcggaatgg gcgatggcgg aaatgatcaa gaatccaaga      1080
gtgcaacaaa aagtgcaaga agagttcgac agagtggttg gacttgaccg gatcttaacc      1140
gaggcagatt tctcccgctt accttacttg caatgcgtgg tgaaagagtc attcaggctg      1200
catcctccaa cgcctctaat gctacctcac cgaagcaacg cagatgtcaa gatcggaggc      1260
tatgatattc ccaaaggatc aaacgttcat gtgaatgtgt gggctgtggc tagagacccg      1320
gctgtatgga aaaatccatt tgagtttaga ccagagagat tcttggaaga agatgttgac      1380
atgaagggtc atgattttag gctgcttccg tttggagctg aagacgggt ttgtcccggt       1440 gcacaacttg gtatcaattt ggtaacttcg atgatgagtc atttgcttca ccattttgtt      1500
tggacacctc ctcaagggac taaaccggag gagattgaca tgtctgaaaa ccctggactc      1560
gttacttaca tgcgtacccc tgtgcaagcg gttgcaacgc ctcggttgcc ttcggatctg      1620
tacaaacgcg tgccttacga tatgtaaatg tcactctgat ctaccttttg ttgctgctgc      1680
tcatgctctt gttgttgttt gtagacatgt ttccttgtggt ttatcatcga aaaacttttg     1740
atgagatttg ttgtatcaat tctctcaagg agaagtaaag aagccatctt ctttgtcatt      1800
gggtttacga tctttcaatc agtgcaatgt tgtaacttga aacataagaa taaacaggaa      1860
acaaacatac aaagatattt gcagg                                            1885

<210> SEQ ID NO 30
<211> LENGTH: 1507
<212> TYPE: DNA
<213> ORGANISM: Nicotiana tabacum

<400> SEQUENCE: 30
tttggaattc atttcaggga attgaaccgg ttgatcaacg atgaagatcg aggtgaaaga       60
atcgacgatg gtaaagccgg cggcggagac gccacaacag aggctgtgga actctaatgt      120
ggatttggtg gtgccgaatt ccacacgcc aagtgtttat ttttacaggc cgacgggatc       180
cccaaatttc ttcgacggaa aagtgctgaa ggaagctcta agcaaagcac ttgtgccgtt      240
ttatcctatg gcggggaggc tgtgtaggga cgaagatggt cgtattgaga ttgactgtaa      300
aggtcagggg gtgcttttg tggaagctga gtcggatggt gtggtggatg attttggtga      360
ttttgccccg acgttagaac tccgtcaact catccccgcc gttgattact cacaaggaat      420
tcaatcgtat gctctcttag tgttgcagat aacacatttt aaatgtgggg gagtttccct      480
tggtgtgggc atgcaacatc atgcagcaga tggagcttct ggtcttcact tcatcaacac      540
atggtctgat atggctcgtg gtctggacct caccatccca cctttcattg accggaccct      600
cctccgtgct cgtgatccac ctcagcctca gtttccccat gtcgagtacc agccacctcc      660
cactctcaag gtaactccag aaaacacccc tatatctgaa gctgttcctg aaaccagcgt      720
gtccatcttc aaattaaccc gtgatcaaat caataccctc aaagcgaagt ccaaggaaga      780
tggaaatacc gttaactaca gctcctacga gatgttggca ggacatgtgt ggcgctccac      840
gtgcatggca cgaggactcg ctcatgatca agaaaccaaa ttgtacatag caacagatgg      900
acgttccagg cttcggccct ctctcccacc aggctatttc ggtaatgtga tatttactac      960
cactcctatt gcagtcgcag gtgatatcca atcgaagcct atttggtatg ctgccagtaa     1020
attacatgat gcattggcta gaatggacaa cgattactta agatcagctc ttgattattt     1080
ggagttgcag cctgacttaa aggctcttgt tcgtggtgca catacgttta agtgcccgaa     1140
tttaggaata actagttggt ctaggctgcc aatccatgat gctgatttg ctgggggtag      1200 gcctatattt atgggacctg gtggtattgc ttatgaaggt ttaagcttta tattgccaag     1260
```

```
tcctacaaat gatggcagtc aatctgttgc aatctctcta caagcagaac acatgaaact   1320
tttcgagaag ttcttgtatg acttttgaaa gaaaccaaat ctttgtgctg cttcttttgg   1380
ggtttatatt gatggatatg taaaagactc cttttatttt ttcattggag gctgttcttt   1440
cttcttcttt ttttcctcag tggaacttcg gtcatattca aatagacat cagttctatt    1500 tctgctt                                                             1507
```

<210> SEQ ID NO 31
<211> LENGTH: 1923
<212> TYPE: DNA
<213> ORGANISM: Medicago truncatula

<400> SEQUENCE: 31

```
actcattctc caaataacaa tttaaggtag ccaaaaccaa attaattagt aattaacaaa     60
ctcaaccatg gggatccttt cctatttgtg ctactctctc ttttatcttt ctatattttt    120
catcattagg cttttgttcc aatcaagaaa attcaaaaac cttccaccag gtccaacttc    180
tcttcctata attggtaacc ttcaccatct caaacgtccc ctaaaccgta cctttaaggc    240
actcactgaa aagtatggta acgtgatttc cctttggttt ggttcacgtc ttgttgtcgt    300
tgtttcttca ctttccgaat tcaagaatg ttttacaaaa aacgacgttg tcctagcaaa     360
tagaccacgg tttttatccg gaaaatatat tttctacaat tacaccactt taggatctac    420
ctcctacggt gaacactggc gtaaccttcg tcgtatcact tcccttgatg ttctttcaaa    480
ccaccgtatc aacaactttg ctcctatccg aagagacgag actcagaggt tgatcaagaa    540
gttggctgaa gattcatcca ctaaatttgc tgaagtagaa cttactttca ggttttcga    600 tatgaccttc aacaacatca tgagaatgat ctctggaaag agatactatg gtgatgattg    660
cgacatatct gaggttcaag aagcaagtca atttagggat atggtatctg aactgttgca    720
gttatcagga gcaaacaata agactgattt catgcccttg ttaaagtttc ttgactttga    780
aaacttggag aagagagtca agcgtattgg tgaaaagaat gatgtatttt tgagtggact    840
ccttcaagag caacgtagca agaaagaacg tacaaatacc atgatagatc atcttctaaa    900
catgcaagaa tcacagccag agtactacac cgatacaatc atcaaaggcc tttgtttggc    960
aatgctcctt gctggaacgg actcatctgc cgtaacatta gagtggacca tgtcaaatat   1020
tttgaactat ccagaggtat tgaaaaggt aagagatgaa gtggatactc atgtaggaca   1080
agatcgtttg gttgatgaat cagaccttcc gaaactaact tacctaagaa atgttatcta   1140
cgagacccct cgattgtata ctcctgctcc attgttatta ccacactcaa ctgcagatga   1200
gtgcattatg ggaggataca agttccgcg cgacaccata gtattgatca atgcttgggc   1260
cattcataga gaccctgaaa catggagtga agccacaact ttcaagccgg agaggttcga   1320
caaaaaagga gagttggaga agatgattgc atttggaatg ggaagaaggg catgtccagg   1380
agaaggttta gctcttcgag caattagcat gacattggca ttattggttc aatgctttga   1440
ttggaaacgt ataacgatg aaaaaattga tatgtcagaa cgagatgggt tcactatgac   1500
aaagttacta ccattgaagg ccatgtgtaa aactcgtccg gtcgtcaaca aggttttcaa   1560
gtaattcatc taaggaaagt caatcaaaaa tgttatatgt actatgttcg catataaatc   1620
atatcatatc atttgtaatt tgttgtcaaa tctgcgtgct caaataattg taatatgtgt   1680
agtgatcggt atgcacatgg atttttctcaa ataaagttt ttatttgtaa ttcttaatat    1740
ctattgtagc cactcaaata attaagtgcg tggaacgtga taagaaacca cttaaataggg   1800 gtagctacaa aataaagaat tagtactatc agagtgagtg ggtacaaaat aaacagttac   1860
```

-continued

```
tgtagactgt agtactaaaa aactttgatg tatgcttacg tacaggtttg tcgttgtctt    1920
tac                                                                  1923

<210> SEQ ID NO 32
<211> LENGTH: 1868
<212> TYPE: DNA
<213> ORGANISM: Medicago truncatula

<400> SEQUENCE: 32
gccttattct attactctct cctttctcta tccttcatca taaccatcaa aattttactc      60
aaaatcacat caagaaggct aaaaaacctt ccaccaggtc caccaacaat tcctataatt     120
ggcaacctcc accacctaaa acaccctctc caccgtacct tcacaaccct atcacaaaca     180
tacggtgaca tcttttcact ttggttcggt tcgcgcctag ttgtcgttgt ttcttccccg     240
tctttagccc atgaatgctt cacaaaaaac gacatcattt tagcgaaccg accacgtttc     300
ctaaccggaa aatacatctt ttacaattac acaaccctag gctccgcttc ttatggggac     360
cattggcgta atctacgtcg tataacaacc attgatgttc tttctaacaa tcgtcttaac     420
tccttcttag gagttcgaag agacgaaaca aatagactta tacaaaagct tctcaaagac     480
gtcgtctctg aaggtttcgg tttcactaaa gtggaactga gaccgagact aacagagatg     540
acgtttaatg ctatgatgag aatgatatcg ggaaaacggt attatggaga tgacggagat     600
gtgtcagatg ttgaagaagc taaacaattt agggagataa taagtgagat gatgtctttg     660
ttaggtgcta ataataaggg tgatttttg cctttgttaa gggtggttga tcttgataat     720
ttggagaaaa ggtgcaagag gattgcaaaa agatctaatg catttttgga gggactcatt     780
gaggaacatc gccgtggaaa tattcatagt gatggaggta caatgattga tcatcttttg     840
aagctaagtg aatcacaacc tgagtattat tcagatcatt tgatcaaagg tctaattcag     900
ggtatgcttc ttgcgggaac agacacatca gcagtgacaa tagaatgggt aatgtctgaa     960
ttgttgaacc acccagaagt attaagaaa gcaaagaag aattagacac tcaaattgga    1020
aaaaacaaat tagtagatga acaagatttg tcaaaacttc catacctaca aaacataatc    1080
tctgaaacac ttagattgca tccaccagct ccactacttt tgccacatta ttcttcagag    1140
gattgcacta ttgagaatt caatgttcca aaagatacta taatattgac caatgtttgg    1200
ggtattcata gagatccaaa acattggaat gatgctttga gttttaaacc agagaggttt    1260
gaaaaagaag aggaggtgaa caaagtaatg gcatttgggt taggaagaag ggcttgtcct    1320
ggattaagct tggcccaacg tactgtgggc tttactgtgg gcttgttgat ccaatgcttt    1380
gaatgggaaa gagagagtga ggaaaaactt gatatgatgg agggtaaagg aattaccatg    1440
ccaatgaaga taccattaag ggctatgtgt aaagcactac ctatagccaa tgatgtaacg    1500
aagtgagaga aatgttatga ataccctctt tttagcattc tttctaatac tcgttttttt    1560
attgggtgaa actcatataa gtctcactat tttatgtgag atccattttc aatgtgtagt    1620
atccacataa atttcatcca ataaacaagt gggtgttaga aaaaacgtta gaaagagatt    1680
gtgtatagca ctcctcgatg aagtgatgcc cttttttggt tacatccaat gataacttat    1740
ctctcagcta gtagaaattg tgtgacgata taatgatatg taaattagac tctatttttc    1800
tccctctata ttatgctctc ctttacttca gagaaagcta ccttatattt aaaaaaaaaa    1860
aaaaaaaa                                                            1868
```

<210> SEQ ID NO 33
<211> LENGTH: 1181
<212> TYPE: DNA
<213> ORGANISM: Medicago sativa

<400> SEQUENCE: 33

| | | | | | |
|---|---|---|---|---|---|
| ctcgaaacaa | gagaaaacag | acacacacat | aaacacactt | gttttttcc | aatggcaact | 60 |
| gaaaacaaaa | tcctcatcct | aggaccaaca | ggagctattg | gaagacacat | agtttgggca | 120 |
| agtattaaag | caggaaatcc | aacatatgct | ttggttagaa | aaacacctgg | caatgttaac | 180 |
| aagccaaagc | ttattacagc | tgctaatcct | gaaaccaagg | aagagcttat | tgataattac | 240 |
| caatctttag | gagttattct | acttgaaggt | gatataaatg | atcatgaaac | tcttgttaag | 300 |
| gcaatcaagc | aagttgacat | tgtgatctgt | gctgctggta | gactactaat | tgaggatcag | 360 |
| gtcaagatta | ttaaagcaat | taaagaagct | ggaaacgtta | agaaattttt | cccatctgaa | 420 |
| tttgggctag | acgtggaccg | tcacgatgca | gttgagccag | ttagacaagt | ttttgaagaa | 480 |
| aaagcaagta | tccgaagagt | aattgaggct | gaaggagttc | cttacactta | cctttgttgc | 540 |
| cacgcctta | ccggttactt | cttacgtaac | ttggctcaac | tggacgccac | tgatcctcct | 600 |
| cgcgacaaag | ttgtcattct | tggagatgga | aatgtgaaag | gagcttatgt | cactgaagct | 660 |
| gatgttggga | cttttaccat | tagagcagca | atgatccca | acacattgaa | caaagctgtc | 720 |
| catattagac | tccccaaaaa | ttatttgacc | caaaatgagg | tcattgctct | tgggagaaa | 780 |
| aagattggga | agactcttga | gaaaacttat | gtttcagagg | aacaagttct | caaggatatt | 840 |
| caagaatctt | cattccctca | taactatttg | ttggcattgt | accattcaca | acaaataaaa | 900 |
| ggagatgcag | tgtatgagat | tgatccagcc | aaagatattg | aagcttctga | agcctatcca | 960 |
| gatgtgcat | acaccactgc | tgatgaatat | ttgaatcaat | ttgtctaacg | aatgctaagg | 1020 |
| aaatgttcaa | taagacaatg | aatttaaaaa | aaaaaaaag | tttcacatct | gtgtatgttt | 1080 |
| cttgtgtttg | tttagtttg | ttctcagtaa | tccctcccaa | ttgatgtaat | aatttacaaa | 1140 |
| aataataaat | attatattct | gttcaaaaaa | aaaaaaaaa | a | | 1181 |

<210> SEQ ID NO 34
<211> LENGTH: 1552
<212> TYPE: DNA
<213> ORGANISM: Arabidopsis thaliana

<400> SEQUENCE: 34

| | | | | | |
|---|---|---|---|---|---|
| tatgtgtcta | tcgttagctt | ctacagctca | acgaaacaca | cagttccgta | gcagagtttt | 60 |
| agttttagca | gagttggtga | aatcaatggg | ccaccaaaac | gccgccgttt | cagagaatca | 120 |
| aaaccatgat | gacggcgctg | cgtcgtcgcc | gggattcaag | ctcgtcggat | tttccaagtt | 180 |
| cgtaagaaag | aatccaaagt | ctgataaatt | caaggttaag | cgcttccatc | acatcgagtt | 240 |
| ctggtgcggc | gacgcaacca | acgtcgctcg | tcgcttctcc | tggggtctgg | ggatgagatt | 300 |
| ctccgccaaa | tccgatcttt | ccaccggaaa | catggttcac | gcctcttacc | tactcacctc | 360 |
| cggtgaccttc | cgattccttt | tcactgctcc | ttactctccg | tctctctccg | ccggagagat | 420 |
| taaaccgaca | accacagctt | ctatcccaag | tttcgatcac | ggctcttgtc | gttccttctt | 480 |
| ctcttcacat | ggtctcggtg | ttagagccgt | tgcgattgaa | gtagaagacg | cagagtcagc | 540 |
| tttctccatc | agtgtagcta | atggcgctat | tccttcgtcg | cctcctatcg | tcctcaatga | 600 |
| agcagttacg | atcgctgagg | ttaaactata | cggcgatgtt | gttctccgat | atgttagtta | 660 |
| caaagcagaa | gataccgaaa | aatccgaatt | cttgccaggg | ttcgagcgtg | tagaggatgc | 720 |

-continued

```
gtcgtcgttc ccattggatt atggtatccg gcggcttgac cacgccgtgg gaaacgttcc      780
tgagcttggt ccggctttaa cttatgtagc ggggttcact ggttttcacc aattcgcaga      840
gttcacagca gacgacgttg gaaccgccga gagcggttta aattcagcgg tcctggctag      900
caatgatgaa atggttcttc taccgattaa cgagccagtg cacggaacaa agaggaagag      960
tcagattcag acgtatttgg aacataacga aggcgcaggg ctacaacatc tggctctgat     1020
gagtgaagac atattcagga ccctgagaga gatgaggaag aggagcagta ttggaggatt     1080
cgacttcatg ccttctcctc cgcctactta ctaccagaat ctcaagaaac gggtcggcga     1140
cgtgctcagc gatgatcaga tcaaggagtg tgaggaatta gggattcttg tagacagaga     1200
tgatcaaggg acgttgcttc aaatcttcac aaaaccacta ggtgacaggc cgacgatatt     1260
tatagagata atccagagag taggatgcat gatgaaagat gaggaaggga aggcttacca     1320
gagtggagga tgtggtggtt ttggcaaagg caatttctct gagctcttca agtccattga     1380
agaatacgaa aagactcttg aagccaaaca gttagtggga tgaacaagaa gaagaaccaa     1440
ctaaaggatt gtgtaattaa tgtaaaactg ttttatctta tcaaaacaat gttatacaac     1500
atctcattta aaaacgagat caatcaaaaa atacaatctt aaattcaaaa cc             1552
```

<210> SEQ ID NO 35
<211> LENGTH: 1658
<212> TYPE: DNA
<213> ORGANISM: Arabidopsis thaliana

<400> SEQUENCE: 35

```
caattctaca gttctcatgc taaaccatat tttttgctct ctgttccttc aaaatcattt       60
ctttctcttc tttgattccc aaagatcact tctttgtctt tgattttga ttttttttct      120
ctctggcgtg aaggaagaag ctttatttca tggagtctct gctctctagt tcttctcttg      180
tttccgctgc tggtgggttt tgttggaaga agcagaatct aaagtccac tctttatcag      240
aaatccgagt tctgcgttgt gattcgagta agttgtcgc aaaaccgaag tttaggaaca      300
atcttgttag gcctgatggt caaggatctt cattgttgtt gtatccaaaa cataagtcga      360
gatttcgggt taatgccact gcgggtcagc ctgaggcttt cgactcgaat agcaaacaga      420
agtcttttag agactcgtta gatgcgtttt acaggttttc taggcctcat acagttattg      480
gcacagtgct tagcatttta tctgtatctt cttagcagt agagaaggtt tctgatatat       540
ctcctttact tttcactggc atcttggagg ctgttgttgc agctctcatg atgaacattt      600
acatagttgg gctaaatcag ttgtctgatg ttgaaataga taaggttaac aagccctatc      660
ttccattggc atcaggagaa tattctgtta acaccggcat tgcaatagta gcttccttct      720
ccatcatgag tttctggctt gggtggattg ttggttcatg gccattgttc tgggctcttt      780
ttgtgagttt catgctcggt actgcatact ctatcaattt gccacttta cggtggaaaa       840
gatttgcatt ggttgcagca atgtgtatcc tcgctgtccg agctattatt gttcaaatcg      900
ccttttatct acatattcag acacatgtgt ttggaagacc aatcttgttc actaggcctc      960
ttatttcgc cactgcgttt atgagctttt tctctgtcgt tattgcattg tttaaggata     1020
tacctgatat cgaaggggat aagatattcg gaatccgatc attctctgta actctgggtc     1080
agaaacgggt gttttggaca tgtgttacac tacttcaaat ggcttacgct gttgcaattc     1140
tagttggagc cacatctcca ttcatatgga gcaaagtcat ctcggttgtg ggtcatgtta     1200
tactcgcaac aactttgtgg gctcgagcta agtccgttga tctgagtagc aaaaccgaaa     1260
taacttcatg ttatatgttc atatggaagc tcttttatgc agagtacttg ctgttacctt     1320
```

```
ttttgaagtg actgacatta gaagagaaga agatggagat aaaagaataa gtcatcacta    1380
tgcttctgtt tttattacaa gttcatgaaa ttaggtagtg aactagtgaa ttagagtttt    1440
attctgaaac atggcagact gcaaaaatat gtcaaagata tgaatttctg ttgggtaaag    1500
aagtctctgc ttgggcaaaa tcttaaggtt cggtgtgttg atataatgct aagcgaagaa    1560
atcgattcta tgtagaaatt tccgaaacta tgtgtaaaca tgtcagaaca tctccattct    1620
atatcttctt ctgcaagaaa gctctgtttt tatcacct                            1658

<210> SEQ ID NO 36
<211> LENGTH: 1242
<212> TYPE: DNA
<213> ORGANISM: Arabidopsis thaliana

<400> SEQUENCE: 36
ggtgagaatt tcagatttca gaaatcgcca tggcttcagt gactctaggt tcatggattg      60
ttgttcacca ccacaatcat catcatccat cttcaatcct taccaaatcc agatccagat     120
cttgtcctat aactcttact aaacccatct cctttcgatc aaaacgcacc gtttcatcat     180
cttcttcaat cgtttcttct tccgttgtta caaaagaaga caatctacgc caatctgaac     240
catcctcttt cgatttcatg tcgtacatca tcaccaaagc cgaattagtc aacaaagctt     300
tagattcagc tgttcctctc cgtgagccac tcaagatcca cgaagcgatg agttactctc     360
ttctcgccgg tggcaaaaga gttagaccag ttctctgcat cgctgcttgt gaactcgtcg     420
gaggtgaaga atcaaccgct atgccagcac gttgcgccgt cgagatgatt cacaccatgt     480
cgttgatcca cgacgatctc ccttgtatgg ataacgacga tctccgccgt ggaaaaccga     540
ccaaccacaa agtgtttggt gaagacgtcg ctgttttagc cggagacgcg cttctctctt     600
tctctttcga gcatttagct tcggcgacga gttctgatgt tgtttctccg gtgagagtgg     660
ttcgagccgt tggagaattg gctaaagcga taggaacaga agggttagtg gcgggtcaag     720
tcgtggatat tagtagtgaa gggttagatt taaacgacgt cggtttagag catttggagt     780
ttatccattt gcataaaacg gcggcgttgc ttgaagcttc tgctgttttg ggagctattg     840
ttggtggagg aagtgatgat gagattgaga ggttaagaaa gtttgcgaga tgtattggtt     900
tgttgtttca ggtggttgat gatatcttgg atgtgacgaa atcgtcgaaa gagttaggga     960
aaactgctgg gaaagatttg attgctgata agttgacgta tcctaagatt atgggtttgg    1020
agaaatcgag agagttttgct gagaaattga atagagaggc tcgtgatcag ctttagggt    1080 ttgattctga taaggttgct cctttgttgg ctttggctaa ttacattgcc tatagacaga    1140 actgattgt gttcgattcc ttttgtcggg aatcattatt agattggaat tgtagaaatc    1200
tcggacaggt tctctagagt ttgttggtgt aatcgtatcc gg                       1242

<210> SEQ ID NO 37
<211> LENGTH: 1308
<212> TYPE: DNA
<213> ORGANISM: Arabidopsis thaliana

<400> SEQUENCE: 37
acatttataa agttctatta gagacggtgg ataggccatg gctactactg ttcatctcag      60
ctcattctcc ctcttcatcc aatccagagg aagaagagac aactccatat cttccgtcaa     120
gagtctcaaa aaacgcacag gtttgtctcc ctcttctgcc ctcacctcac aaggtggcag     180
agacatgatt ccaccagagg gaaaatgcaa tgatcacaac tctgcttttg atttcaagtt     240
gtatatgatc cgcaaagccg aatctgtaaa tgcggctctc gacgtttctg taccgctccg     300
```

-continued

```
agaacccctc actgtccagg aagccgtgcg gtactcattg ctagcgggcg gaaaacgtgt    360
gaggcctctg ctctgcattg ccgtctgcga gcttgtggga ggcgacgagg ctactgccat    420
gtcagctgct tgcgcggttg agatgatcca cacaagctct cttattcatg acgatcttcc    480
gtgcatggac aatgccgacc tccgcagagg caagcccacc aaccacaagg tatatggaga    540
agacatggcg gttttggcag gtgatgcact ccttgcattg gcgtttgagc acatgacggt    600
tgtgtcgagt gggttggtcg ctcccgagag gatgattcgc gcggtggttg agctggccag    660
ggccataggg actacagggc tagttgctgg acaaatgata gacctagcca gcgaaagact    720
gaatccagac aaggttggat tggagcatct agagttcatc catctccaca aaacggcggc    780
attgttggag gcagcggcgg ttttagggg tataatggga ggtggaacag aggaagagat     840
cgaaaagctt agaaagtatg ctaggtgtat tggactactg tttcaggtgg ttgatgacat    900
tctcgacgta acaaaatcta ctgaggaatt gggaagagact gcaggaaaag acgtaatggc    960
tggaaagctg acgtatccaa ggctgatagg tttggagaga tcaaaggaag ttgcagagaa   1020
actgaggaga gaagcagagg aacaacttct agggtttgat ccaagtaagg cggcgcctct   1080
ggtggctctt gctagctaca tcgcttgcag acacaactga atggactgat catatcctca   1140
atgcatcaat ctcctaacaa gtccttttac ttagatctat ggtcttgttt cttataaatc   1200
atctatgccg tgtgatcatc tctctcattt gttttcaagt tgtattatgt ttttgaatct   1260
taataatgta atgttcgaaa aatatcaata agatttgctc ataggaac               1308
```

<210> SEQ ID NO 38
<211> LENGTH: 1703
<212> TYPE: DNA
<213> ORGANISM: Arabidopsis thaliana

<400> SEQUENCE: 38

```
cttgaggatc ttctcacatt aatgggtcaa acctttgct cttccttttg attaatttag      60
tgtttgacaa tctcctcctc cttctccttc ttcttcaaag ttttgtcgca gtatctattg    120
ttcttacaga gagaaaggaa agctttagtc ttttaccagt ttgatccaat tctgggtttc    180
actgaaaaaa agttgggagt tgattcttc taactgtaga agaaacagag tcaacagaag    240
aaaactaaaa aagttgagat ttttctctca cgcgctcaac agcttgagta tgtcttcttc    300
tgtagcagtg ttatgggttg ctacttcttc tctaaatcca gacccaatga acaattgtgg    360
gttggtaagg gttctagaat cttctagact gttctctcct tgtcagaatc agagactaaa    420
caaaggtaag aagaagcaga taccaacttg gagttcttct tttgtaatga accgaagtag    480
aagaattggt gttgtgtctt caagcttagt agcaagtcct tctggagaga tagctctttc    540
atctgaagag aaggtttaca atgttgtgtt gaaacaagct gctttggtga acaaacagct    600
aaggtcttct tcttatgatc ttgatgtgaa gaaccacaa gatgttgttc ttcctgggag    660
tttgagtttg ttgggtgaag cttatgatcg atgcggtgaa gtttgcgctg aatatgctaa    720
gacgttttat cttggaactt tgcttatgac acccgaaagg cgaaaggcga tttgggctat    780
ctacgtttgg tgtagaagaa ctgatgaact tgtggatggg ccaaatgctt cacatataac    840
tcccatggct ttagatagat gggaagcaag gttagaagat ctttccgtg gtcgtccttt     900 cgatatgctt gatgctgctc tcgctgatac agttgctaga tacccctgcg atattcagcc    960
atttcgagac atgatcgaag gaatgagaat ggacttgaag aaatcgagat accagaactt   1020
cgatgatcta tacctttact gctactacgt cgctggaacc gtcggattga tgagcgttcc   1080
ggttatggga atcgatccta agtcgaaagc aacaaccgaa agtgtttaca acgctgcctt   1140
```

-continued

```
ggcccttggt atagccaatc agcttactaa catactcaga gacgtaggcg aagatgcgag    1200
aagaggaagg gtttatctgc ctcaggatga attggctcag gctggtcttt cagatgaaga    1260
catattcgcc ggaaaagtaa ctgataaatg gagaaacttc atgaaaatgc agcttaaacg    1320
agcaagaatg ttcttcgacg aagctgagaa aggcgtcacc gagctcagtg ccgctagcag    1380
atggcctgta tgggcttcat tgctattgta caggagaata ctggacgaga ttgaagcgaa    1440
tgattacaac aattttacta agagagctta tgtggggaaa gtcaagaaaa ttgcagcttt    1500
gccattggct tatgctaaat cagtactaaa gacttcaagt tcaagactat cgatatgaga    1560
gcgagaggaa agtggaacaa aaacaaccta agagcgcttt ttgtgattaa gaaaaaacta    1620
gggtcgaatt tattatgtta actaatatat acatattaat ggggaagcaa attcttataa    1680
tgttacatta tctttctgaa tgc                                            1703
```

METHODS AND COMPOSITIONS FOR MODIFYING PLANT BIOSYNTHETIC PATHWAYS

The present application claims the priority of U.S. Provisional Application Ser. No. 60/772,354, filed Feb. 9, 2006, the entire contents of which are hereby incorporated by reference.

BACKGROUND OF THE INVENTION

1. Field of the Invention

The present invention relates generally to the field of molecular biology. More specifically, the invention relates to methods and compositions for modifying plant biosynthetic pathways.

2. Description of the Related Art

Plants are capable of synthesizing a large variety of low molecular weight organic compounds, which are collectively called secondary metabolites. In contrast to primary metabolites that are common to all plants, many secondary metabolites are differentially distributed among limited taxonomic groups within the plant kingdom. Plant secondary metabolites play important roles in plant-environment interactions, and in human nutrition and medicine (DellaPenna 1999; Dixon, 2001; La Camera et al., 2004). Secondary metabolites usually exist in low abundance in plants. Because of the structural complexity of secondary metabolites, their chemical synthesis is not only difficult and expensive, but also often results in low yields. It is therefore desirable to be able to manipulate biosynthetic pathways for large-scale production of targeted secondary metabolites in plants, such as by enhancing the expression of endogenous genes or by introducing foreign genes (Dixon, 2005; Galili and Hofgen, 2002; Thelen and Ohlrogge 2002).

Phenylpropanoids are one of the largest groups of plant secondary metabolites, and are synthesized from the aromatic amino acid L-phenylalanine. Isoflavonoids are derived from the phenylpropanoid pathway and are distributed predominantly in the Leguminosae. They were initially recognized for their roles in plant disease resistance and induction of nodulation (Dixon, 2001). They have also received much attention in recent years due to their estrogenic, antioxidant, and anti-cancer activities in humans (Cornwell et al., 2004; Dixon and Ferreira, 2002; Dixon, 2004). It is desirable, in the long term, to be able to produce isoflavonoids in a wide range of plants and crops besides legumes for dietary disease prevention.

In nature, enzymes have often evolved as multi-domain proteins in order to perform tasks that require more than one function. Nature's strategy has been adopted by scientists from different disciplines, in particular *E. coli* and yeast researchers, to develop recombinant multifunctional proteins (Bülow, 1990; James and Viola, 2002; Nixon et al., 1998). However, this approach has not yet been broadly applicable to plants (Tian and Dixon, 2006), whose secondary metabolism presents a more complicated biochemical context than yeast or *E. coli*. An in-frame fusion of thiolase and reductase genes was recently constructed for polyhydroxybutyrate biosynthesis in *Arabidopsis* (Kourtz et al., 2005). The fusion protein exhibited thiolase and reductase activities in *E. coli*, though plants transformed with this construct produced less polyhydroxybutyrate than plants expressing thiolase and reductase individually.

While the foregoing studies have provided a further understanding of the biosynthesis of plant secondary metabolites, methods for the efficient modification of most secondary metabolites have been lacking. This has been particularly true in the case of isoflavonoid biosynthesis. There, therefore, remains a great need in the art for the development of methods and compositions that would increase the efficiency by which isoflavonoid biosynthesis can be modified in plants.

SUMMARY OF THE INVENTION

In one aspect, the invention provides a DNA construct comprising a promoter functional in a plant operably linked to a nucleic acid sequence encoding a fusion polypeptide comprising a first enzyme and a second enzyme, wherein the first enzyme is a membrane-bound enzyme, such as a cytochrome P450 enzyme, and the second enzyme is a soluble enzyme, wherein the fusion polypeptide comprises the enzymatic activity of the first and second enzymes, and wherein the first enzyme has as a substrate a product of the second enzyme or wherein the second enzyme has as a substrate a product of the first enzyme. In one embodiment, the first enzyme and second enzyme are a pair selected from the group consisting of isoflavone synthase and chalcone isomerase, cinnamate 4-hydroxylase and phenylalanine ammonia-lyase, coumarate 3-hydroxylase and hydroxycinnamoyl CoA quinate/shikimate hydroxycinnamoyl transferase, ferulate 5-hydroxylase and caffeic acid O-methyltransferase, isoflavone 2'-hydroxylase (CYP81E7) or isoflavone 3'-hydroxylase (CYP81E9) and isoflavone reductase, CYP79A1 and CYP71E1, geranylgeranylpyrophosphate synthase and phytoene synthase, or 4-hydroxyphenylpyruvate dioxygenase and homogentisate phytyltransferase.

In particular embodiments of the invention, a fusion is provided encoding first and second isoflavone biosynthetic enzymes. In further embodiments, the first and second biosynthetic enzymes are cinnamate 4-hydroxylase and phenylalanine ammonia-lyase or isoflavone synthase and chalcone isomerase. A cytochrome P450 enzyme in specific embodiments, including isoflavone synthase, may be located proximate to the N-terminus of the fusion polypeptide relative to the second enzyme, which may be a soluble enzyme such as chalcone isomerase. An enzyme in a fusion of the invention may be defined as from a legume. In one embodiment, an isoflavone synthase is from soybean and in another embodiment, chalcone isomerase is from alfalfa. In a fusion of the invention, the first enzyme may be fused to the second enzyme via a peptide linker.

In another aspect, the invention provides a recombinant vector comprising a DNA construct as described herein. The recombinant vector may comprise at least one additional sequence chosen from the group consisting of: a regulatory sequence, a selectable marker, a leader sequence and a terminator. In certain embodiments, the additional sequence is a heterologous sequence. The promoter may be a plant developmentally-regulated, organelle-specific, inducible, tissue-specific, constitutive, cell-specific, seed specific, or germination-specific promoter.

In yet another aspect, the invention provides a plant or plant cell transformed with a construct described herein. The plant may be a monocotyledonous or dicotyledonous plant. Parts of the plant are also provided, including a seed of the plant and any composition derived from the plant, such as a food or commodity product.

In yet another aspect, the invention provides a method of modifying the isoflavone biosynthesis of a plant, comprising introducing into the plant a construct of the invention comprising an isoflavone biosynthesis enzyme. In particular embodiments, introducing the coding sequence may comprise plant breeding and/or genetic transformation. In the method, genistein and/or daidzein may be increased in the plant relative to a plant of the same genotype as said plant that lacks the construct. In further aspects, genistein may be increased by at least 15% relative to said plant that lacks the construct.

In still yet another aspect, the invention provides a method of producing food or feed, comprising, a) obtaining a plant of the invention or a part thereof, and (b) producing food or feed from the plant or part thereof. In certain embodiments, the food or feed comprises grain, silage, oil, protein, meal, flour, or starch, or an isoflavone preparation derived from the plant or part thereof. The invention also provides the food or feed. In certain embodiments, the food or feed may be defined as comprising a detectable nucleic acid according to the invention. Further provided by the invention is a nutraceutical composition prepared from a plant or part thereof of the invention.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 7. Protein sequence alignment between soybean IFS and rabbit CYP2C5. Identical amino acids are shaded in black, similar amino acids (conservative substitutions) in grey.

DETAILED DESCRIPTION OF THE INVENTION

The invention overcomes the limitations of the prior art by providing improved methods for the modification of plant biosynthetic pathways as well as for enabling the production of isoflavonoids in plants that do not normally produce isoflavonoids. It was surprisingly shown, for example, that the isoflavonoid biosynthetic genes isoflavone synthase (IFS) and chalcone isomerase (CHI) could be used to generate a bifunctional IFS/CHI enzyme via in-frame gene fusion. The sequence of the fusion is provided in SEQ ID NO:20. A 3-D model of IFS/CHI was constructed and guided design of the fusion protein and allowed optimization of catalytic properties and subcellular localization of the component enzymes. The bifunctional enzyme surprisingly exhibited increased activity in relation to isoflavone formation in planta relative to the activity of the IFS transgene alone. Activity of the bifunctional enzyme was confirmed in yeast and tobacco.

Petals and young leaves of IFS/CHI transgenic tobacco plants were demonstrated to produce higher levels of the isoflavone genistein and genistein glycosides as a ratio of total flavonoids produced than plants transformed with IFS alone. Thus, the ability to increase accumulation of isoflavonoid compounds in non-legume plants was illustrated. In addition to functional benefits, the techniques of the invention simplify transformation of plants with multiple pathway genes, and thus has broad applicability, for example, in connection with genes from the cytochrome P450 family and biochemical pathway engineering.

Figure 1:
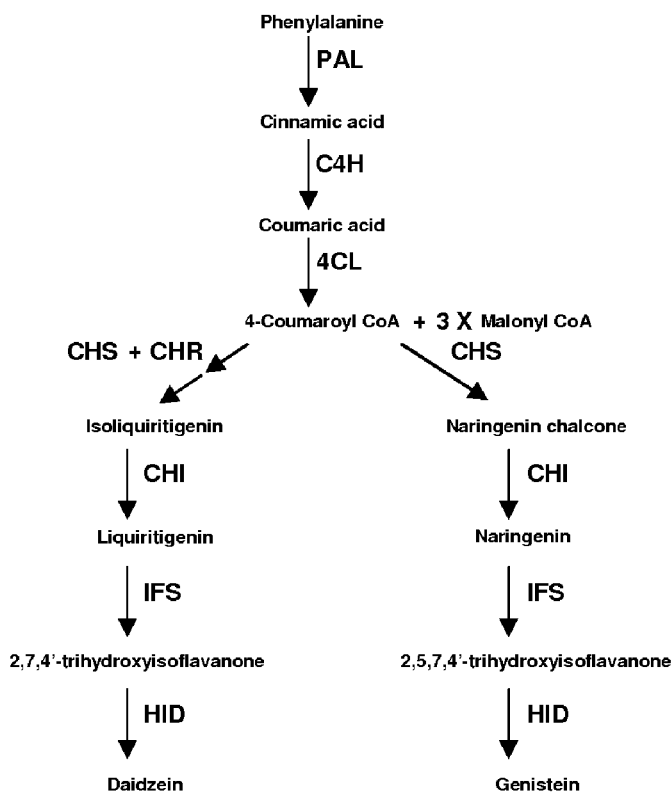
FIG. 1. Isoflavone biosynthetic pathway in legumes. Enzymes are: PAL, L-phenylalanine ammonia-lyase; C4H, cinnamate 4-hydroxylase; 4CL, 4-coumarate CoA ligase; CHS, chalcone synthase; CHR, chalcone reductase; CHI, chalcone isomerase; IFS, isoflavone synthase; HID, 2-hydroxyisoflavanone dehydratase.
Figure 2:
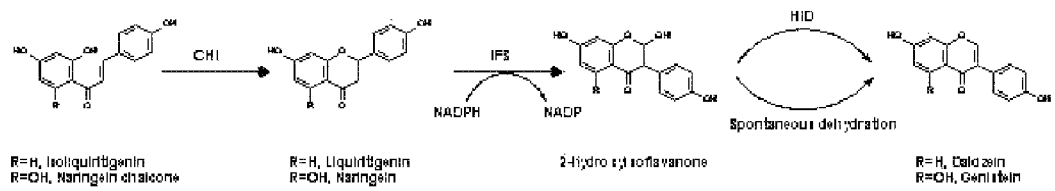
FIG. 2. Construction of IFS/CHI fusion protein (SEQ ID NO:20). (A) Enzyme catalyzed conversion of chalcone to isoflavone: CHI, chalcone isomerase; IFS, isoflavone synthase; HID, 2-hydroxyisoflavanone dehydratase. (B) Schematic illustration of IFS/CHI fusion protein. The 5' end of the alfalfa CHI coding sequence was fused in-frame to the 3' end of the soybean IFS coding sequence via a Gly-Ser-Gly linker. (C) Graphic simulation of the three-dimensional structure of the IFS/CHI fusion protein. Strands are shown as arrows with arrow heads pointing to their C-termini. Helices are represented as ribbons. The heme group of IFS and the product of CHI (2S-naringenin) are shown as ball-and-sticks. The location of the Gly-Ser-Gly (G-S-G) linker is indicated.
Figure 2:
Figure 2:
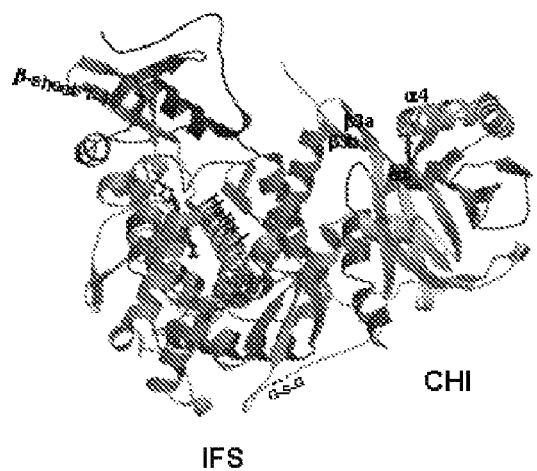

The engineering of isoflavonoid biosynthesis in plants is of particular importance due to the numerous health and other benefits that have been associated with plant isoflavonoid secondary metabolites. In plants, isoflavonoids share common biosynthetic precursors, the chalcones, with other phenylpropanoid compounds such as aurones, flavones and anthocyanins. Chalcones are polyketides that are synthesized via the addition of three malonyl groups to coumarate by chalcone synthase (CHS) (FIG. 1). Chalcone isomerase (CHI) catalyzes the cyclization of chalcone to form flavanone. The first committed step for isoflavonoid biosynthesis is a unique aryl migration reaction catalyzed by a cytochrome P450 enzyme CYP93C1, the isoflavone synthase (IFS) (FIG. 2A). The immediate product of the IFS reaction is 2-hydroxyisoflavanone, which can be dehydrated to isoflavones either spontaneously or through catalysis by 2-hydroxyisoflavanone dehydratase (FIG. 2A; Akashi et al., 2005). Genistein is the end product of the isoflavone synthase and 2-hydroxyisoflavanone dehydratase reactions when naringenin is used as substrate (FIG. 1).

Genistein is well-known for its phytoestrogenic activities (Barnes, 2004; Dixon and Ferreira, 2002), but is also a building block for many structurally more complicated isoflavonoid compounds. Most plant species accumulate flavonoids and anthocyanins, hence their biosynthetic precursor, chalcone, is available as a substrate for introducing the isoflavonoid pathway into non-legume plants.

In certain embodiments, the invention therefore provides a method of modifying plant isoflavonoid biosynthesis comprising introducing into the plant a nucleic acid encoding one or more bifunctional fusion peptide(s) comprised of first and second isoflavonoid biosynthesis enzymes. The fusion polypeptide may be created by fusing first and second isoflavonoid biosynthesis coding sequences, for example, selected from any combination of L-phenylalanine ammonia-lyase (PAL); cinnamate 4-hydroxylase (C4H); 4-coumarate CoA ligase (4CL); chalcone synthase (CHS); chalcone reductase (CHR); chalcone isomerase (CHI); isoflavone synthase (IFS); and 2-hydroxyisoflavanone dehydratase (HID).

I. PLANT EXPRESSION CONSTRUCTS AND NUCLEIC ACIDS

In one aspect of the invention, plant transformation vectors comprising a nucleic acid encoding a bifunctional fusion polypeptide are provided. An exemplary construct according to the invention comprises a promoter functional in a plant operably linked to a nucleic acid sequence encoding a fusion polypeptide comprising a first enzyme and a second enzyme, wherein the first enzyme is a membrane-bound enzyme, such as a cytochrome P450, and the second enzyme is a soluble enzyme.

In particular embodiments of the invention, the first enzyme and second enzyme are a pair selected from the group consisting of isoflavone synthase and chalcone isomerase, cinnamate 4-hydroxylase (see, e.g., GenBank Accession #AY641731; SEQ ID NO:26) and phenylalanine ammonialyase (see, e.g., GenBank Accession #D17467; SEQ ID NO:25), coumarate 3-hydroxylase (see, e.g., GenBank Accession # NM 180006; Schoch et al., 2001; SEQ ID NO:29) and hydroxycinnamoyl CoA quinate/shikimate hydroxycinnamoyl transferase (see, e.g., GenBank Accession # AJ507825; Hoffmann et al., 2003; SEQ ID NO:30), ferulate 5,-hydroxylase (see, e.g., GenBank Accession # DQ222911; Reddy et al., 2005; SEQ ID NO:27) and caffeic acid O-methyltransferase (see, e.g., GenBank accession #M63853; Gowri et al., 1991; SEQ ID NO:28), or isoflavone 2'-hydroxylase or isoflavone 3'-hydroxylase (see, e.g., GenBank Accession #s AY278227 and AY278228 respectively; Liu et al., 2003; SEQ ID NOs:31-32) and isoflavone reductase (see, e.g., GenBank Accession # X58078; Paiva et al., 1991; SEQ ID NO:33) For example, a cinnamate 4-hydroxylase fusion with L-phenylalanine ammonia-lyase may be used for improving flux into the overall phenylpropanoid pathway, a coumarate 3-hydroxylase fusion with hydroxycinnamoyl CoA quinate/shikimate hydroxycinnamoyl transferase may be used for improving flux into guaiacyl and syringyl lignin, a ferulate 5-hydroxylase fusion with caffeic acid 3-O-methyltransferase may be used for improving flux into syringyl lignin, and an isoflavone 2'-hydroxylase or isoflavone 3'-hydroxylase fusion to isoflavone reductase may be used for improving flux into the production of pterocarpanoid phytoalexins. A bifunctional fusion peptide between geranylgeranylpyrophosphate synthase (GGPPS; e.g. SEQ ID NO:36 or SEQ ID NO:37) and phytoene synthase (PSY; e.g. SEQ ID NO:38) can also be constructed to allow for modification of carotenoid content in plants and/or cell cultures. Likewise, an artificial bifunctional tocopherol biosynthetic enzyme, 4-hydroxyphenylpyruvate dioxygenase (HPPD; e.g. SEQ ID NO:34)/homogentisate phytyltransferase (HPT; e.g. SEQ ID NO:35), will lead to changes in tocopherol quantity in plants. These coding sequences are well known in the art.

In one embodiment of the invention, a fusion polypeptide is therefore provided that comprises an enzyme coding sequence or the polypeptide encoded thereby set forth in the Sequence Listing, as well as polypeptides and fragments thereof, particularly those polypeptides which exhibit enzyme activity have at least 85%, more preferably at least 90% identity, and most preferably at least 95% identity to a polypeptide sequence selected from the group of sequences set forth in the Sequence Listing. "Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Computational Molecular Biology, Lesk, A. M., ed., Oxford University Press, New York (1988); Biocomputing: Informatics and Genome Projects, Smith, D. W., ed., Academic Press, New York, 1993; Computer Analysis of Sequence Data, Part I, Griffin, A. M. and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., Stockton Press, New York (1991); and Carillo, H., and Lipman, D., SIAM J Applied Math, 48:1073 (1988). Computer programs can be used to determine "identity" between two sequences these programs include but are not limited to, GCG (Devereux, J., et al., Nucleic Acids Research 12(1):387 (1984); suite of five BLAST programs, three designed for nucleotide sequences queries (BLASTN, BLASTX, and TBLASTX) and two designed for protein sequence queries (BLASTP and TBLASTN) (Coulson, Trends in Biotechnology, 12: 76-80 (1994); Birren, et al., Genome Analysis, 1: 543-559 (1997)). The BLAST X program is publicly available from NCBI and other sources (BLAST Manual, Altschul, S., et al., NCBI NLM NIH, Bethesda, Md. 20894; Altschul, S., et al., J. Mol. Biol., 215:403-410 (1990)). The well known Smith Waterman algorithm can also be used to determine identity.

Parameters for polypeptide sequence comparison include the following: Algorithm: Needleman and Wunsch, *J. Mol. Biol.* 48:443-453 (1970); Comparison matrix: BLOSSUM62 from Hentikoff and Hentikoff, *Proc. Natl. Acad. Sci. USA* 89:10915-10919 (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for polynucleotide sequence comparison include the following: Algorithm: Needleman and Wunsch, *J. Mol. Biol.* 48:443-453 (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

In specific embodiments of the invention, a bifunctional fusion polypeptide is therefore provided that is defined as comprising a first domain and a second domain, wherein the first and second domains comprise first and second isoflavonoid biosynthesis enzymes, specifically including biosynthetically active fragments of a native enzyme. The first and second domains may, in one embodiment, be joined by a peptide linker sequence. The linker sequence may provide additional flexibility between the two enzymes and thus avoid steric hindrance and enhance activity. In one embodiment, the linker may comprise, for example, about 3-10 amino acids linking the first and second domains.

The invention therefore provides nucleic acids encoding a fusion polypeptide described herein. The nucleic acid may be defined as comprising nucleic acids encoding, in frame, the first and second domains. A coding sequence for a linker peptide may in addition optionally be included. Those of skill in the art will understand in view of the disclosure that such nucleic acids may be provided as an expression construct by linking appropriate regulatory elements to the nucleic acid corresponding to a host cell in which heterologous expression is desired. For plant expression, a plant promoter may be operably linked to the nucleic acid. In addition, other elements such as enhancers, terminators and transit peptides may be used. Endogenous or heterologous elements may be used. For example, IFS could be placed at the N-terminus of the encoded polypeptide in order to utilize a native endoplasmic reticulum localization peptide.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with coding sequences that alter plant secondary metabolite biosynthesis as described herein. The coding sequences may be provided with other sequences such as regulatory elements or other coding sequences. Where a selectable or screenable marker is used, one may employ the separate coding regions on either the same or different DNA segments for transformation. In the latter case, the different vectors are delivered concurrently to recipient cells to maximize cotransformation.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise coding sequence which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components that may be included with plant transformation vectors are as follows.

A. Regulatory Elements

Exemplary promoters for expression of a nucleic acid sequence in plants include the CaMV 35S promoter (Odell et al., 1985), CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al, 1989), PEPCase (Hudspeth and Grula, 1989) or R gene complex associated promoters (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the native promoter of a isoflavone biosynthesis sequence is used. In another embodiment, a heterologous sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that nucleic acids encoding a fusion polypeptide as provided herein may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. Alternatively, a heterologous 3' end may enhance the expression of coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyro sine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; or a gene encoding for green fluorescent protein (Sheen et al., 1995; Haseloff et al., 1997; Reichel et al., 1996; Tian et al., 1997; WO 97/41228).

II. METHODS FOR GENETIC TRANSFORMATION

Suitable methods for transformation of plant or other cells for use with the current invention are believed to include virtually any method by which DNA can be introduced into a cell, such as by direct delivery of DNA such as by PEG-mediated transformation of protop lasts (Omirulleh et al., 1993), by desiccation/inhibition-mediated DNA uptake (Potrykus et al., 1985), by electroporation (U.S. Pat. No. 5,384, 253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464, 765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al, 1998) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S.

Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al, 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant lines that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety (Thompson, 1995), and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

III. PRODUCTION AND CHARACTERIZATION OF STABLY TRANSFORMED PLANTS

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed.

One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use a bar-bialaphos or the EPSPS-glyphosate selective system, for example, transformed tissue can be cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate may be preferred, it is proposed that ranges of 0.1-50 mg/l bialaphos or 0.1-50 mM glyphosate will find utility.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}M$ abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discrete fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. BREEDING PLANTS OF THE INVENTION

In addition to direct transformation of a particular plant genotype with a construct prepared according to the current invention, transgenic plants may be made by crossing a plant having a selected DNA of the invention to a second plant lacking the construct. For example, a selected fusion polypeptide coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

V. DEFINITIONS

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VI. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Computer Modeling of an IFS/CHI Fusion Enzyme

Figure 7:
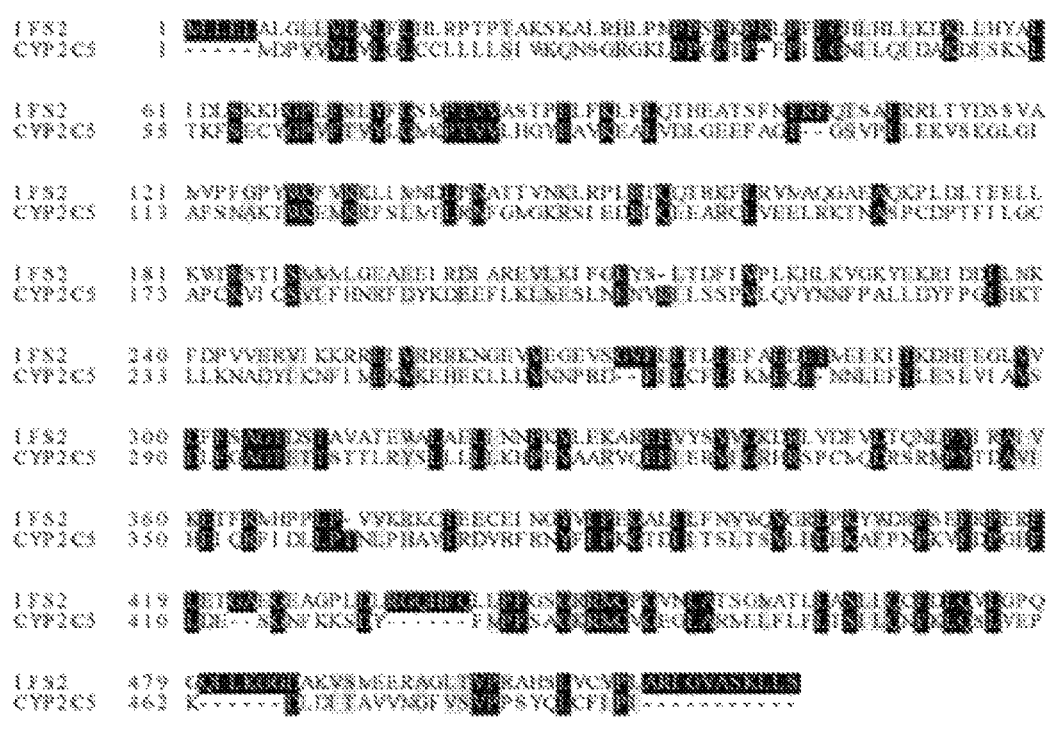

Soybean isoflavone synthase (IFS) is an endoplasmic reticulum (ER)-localized cytochrome P450 enzyme whereas alfalfa chalcone isomerase (CHI) is localized in the cytoplasm (Bednar and Hadcock, 1988; Kochs and Griesbach, 1986). To allow for ER membrane localization of IFS and its required interaction with the membrane-associated NADPH-cytochrome P450 reductase, IFS (SEQ ID NO:22) was placed as the N-terminus of the fusion enzyme to preserve its ER-targeting membrane anchor (FIGS. 2A, B). As shown from the sequence alignment (FIG. 7), IFS is 15 amino acids longer than CYP2C5 at the C-terminus. This gives IFS extra flexibility at the C-terminus. In order to visualize whether the IFS/CHI protein could be folded correctly in vivo, the 3-D structures of IFS and CHI (Jez et al., 2000) were linked in silico at the C-terminus of IFS and N-terminus of CHI (SEQ ID NO:21) to simulate the in vivo in-frame fusion of the two enzymes (FIG. 2C). The 3-D structure of IFS was obtained by homology modeling using the mammalian microsomal cytochrome P450 enzyme CYP2C5 as a template (Williams et al., 2000). The tertiary structure of the fusion protein shows a flexible connection between IFS and CHI, because of which the polypeptide chain can fold into distinct compact regions (FIG. 2C). A three amino acid linker peptide, Gly-Ser-Gly, was added between IFS and CHI to reinforce the flexibility of this connection (FIG. 2B), and this further favors correct conformation and independent action of the joined functional domains.

Example 2

ER-Localization of the IFS/CHI Fusion Protein in Tobacco Epidermal Cells

Figure 3:
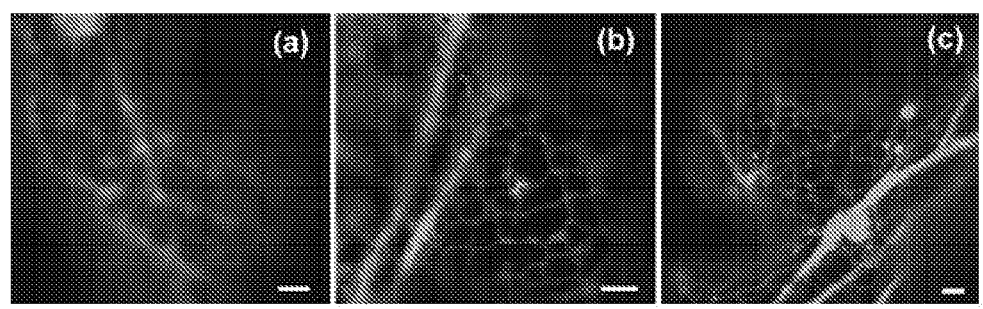
FIG. 3. Confocal images of tobacco leaf epidermal cells transfected with EGFP fusion proteins by particle bombardment. (A) EGFP. (B) Cinnamate 4-hydroxylase transmembrane domain (C4H MA)-EGFP. (C) IFS/CHI-EGFP. Bars=5 µm.

To investigate whether the IFS/CHI fusion protein locates correctly to the ER, enhanced green fluorescent protein (EGFP; SEQ ID NO:23) was attached to the C-terminus of the IFS/CHI fusion to produce an IFS/CHI-EGFP construct. The coding sequence of the construct generated is provided as SEQ ID NO:24. Cinnamate 4-hydroxylase (C4H) is a biosynthetic cytochrome P450 enzyme in the early phenylpropanoid pathway and has been shown to be ER-membrane bound (Ro et al., 2001). The C4H membrane anchor region (C4H MA), which directs the enzyme to the cytosolic face of the ER, was fused to the N-terminus of EGFP and used as a positive control for ER-localization. Open reading frames of IFS/CHI-EGFP, C4H MA-EGFP (Achnine et al., 2004; Fahrendorf and Dixon, 1993), and free EGFP were subcloned into the pRTL2 vector under the control of a double 35S promoter and independently transfected into young tobacco (*Nicotiana tabacum*) leaves through particle bombardment. Green fluorescence was visualized by laser scanning confocal microscopy. Confocal images of transfected tobacco leaf epidermal cells showed that both the C4H MA-EGFP protein and the IFS/CHI-EGFP protein were localized to the ER, as indicated by the fine reticulate localization of fluorescence, whereas free EGFP protein was localized to broader cytoplasmic strands (FIG. 3).

Example 3

Functional Analysis of Recombinant Proteins in Yeast

To determine whether the IFS/CHI fusion protein was functional in vitro, open reading frames encoding IFS, CHI and the IFS/CHI fusion were each subcloned, in *E. coli*, into the yeast expression vector pYeDP60 under the control of a galactose inducible promoter, and the resulting construct was introduced into yeast cells. The yeast WAT11 strain has been engineered to express ATR1, the *Arabidopsis* NADPH-cytochrome P450 reductase, in place of the native NADPH-cytochrome P450 reductase (Pompon et al., 1996), and was used as a host for expression of the single and fused proteins.

Microsomal fractions from WAT11 transformed with pYeDP60 vector control, soybean IFS, alfalfa CHI, or soybean IFS/alfalfa CHI fusion were isolated and tested for enzymatic activities using isoliquiritigenin, liquiritigenin, naringenin chalcone and naringenin as substrates, in the presence (FIG. 4A-D) or absence (FIG. 4E-H) of NADPH. Reaction products were separated by high performance liquid chromatography (HPLC) and their identity confirmed by retention time and UV spectrum compared to those of authentic standards. When incubated with isoliquiritigenin (a substrate for alfalfa CHI) without NADPH, liquiritigenin, the product of the CHI reaction, was produced in microsomes from cells expressing the IFS/CHI fusion protein (FIG. 4D), indicating that the CHI enzyme in the IFS/CHI fusion protein was functional. Microsomes from WAT11 expressing the pYeDP60-CHI construct also converted isoliquiritigenin to liquiritigenin (FIG. 4B), whereas microsomes from cells harboring pYeDP60-IFS or pYeDP60 did not exhibit any activity towards isoliquiritigenin (FIGS. 4A,C).

Figure 4:
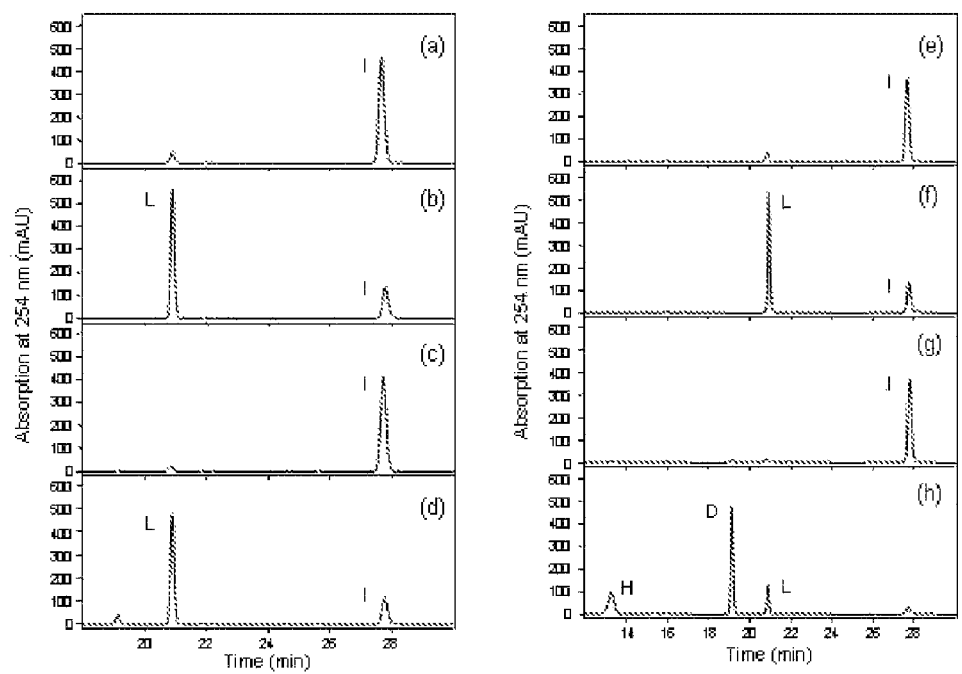
FIG. 4. CHI and coupled CHI/IFS activity of enzymes expressed in yeast. Microsomes were isolated from cells expressing pYeDP60 vector (A, E), alfalfa CHI (B, F), soybean IFS(C, G), and soybean IFS/alfalfa CHI fusion protein (D, H). Isoliquiritigenin was used as substrate and the reaction mixture was incubated with (E-H) or without (A-D) NADPH. Products were analyzed by HPLC. I, isoliquiritigenin; L, liquiritigenin; D, daidzein; H, 2,7,4'-trihydroxyisoflavanone.

When microsomes from pYeDP60-IFS/CHI transformed yeast cells were incubated with isoliquiritigenin and NADPH, a required reductant for the IFS reaction, the major additional product daidzein was observed, along with a smaller amount of 2,7,4'-trihydroxyisoflavanone (FIG. 4H). This indicated that liquiritigenin produced by the CHI reaction was further converted to 2,7,4'-trihydroxyisoflavanone by the functional IFS enzyme in the IFS/CHI fusion protein construct and that this latter compound was then non-enzymatically dehydrated to daidzein. No daidzein was observed on incubation of isoliquiritigenin and NADPH with microsomes expressing IFS alone, CHI, or empty vector (FIGS. 4E-G).

Figure 5:
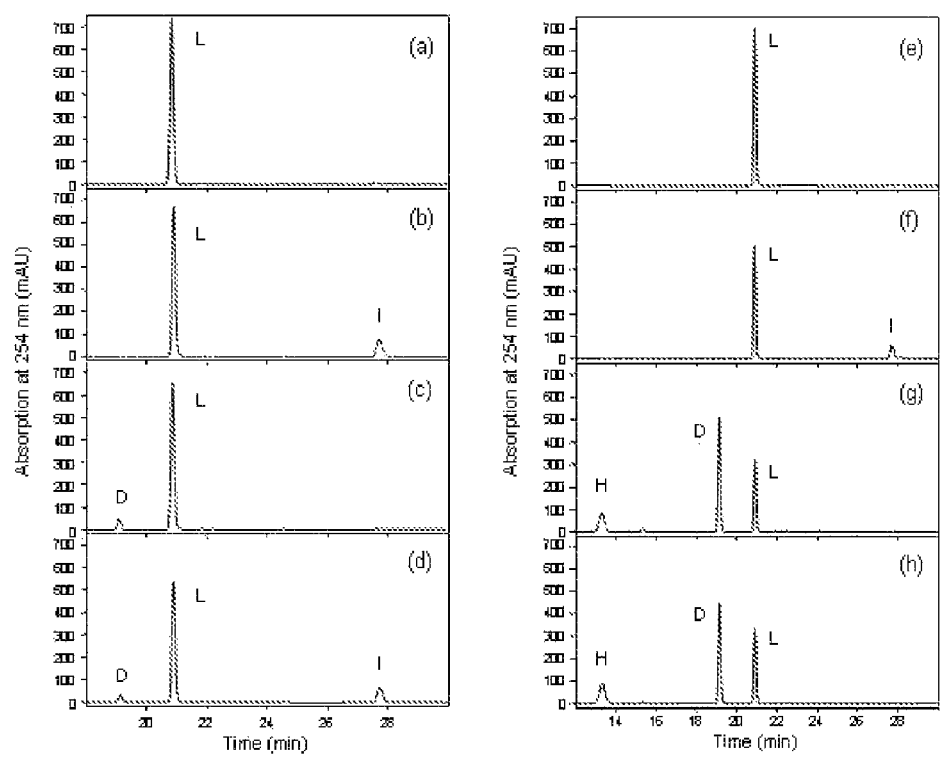
FIG. 5. IFS activity of enzymes expressed in yeast. Microsomes were isolated from cells expressing pYeDP60 vector (A, E), alfalfa CHI (B, F), soybean IFS(C, G), and soybean IFS/alfalfa CHI fusion protein (D, H). Liquiritigenin was used as substrate and the reaction mixture was incubated with (E-H) or without (A-D) NADPH. Products were analyzed by HPLC. I, isoliquiritigenin; L, liquiritigenin; D, daidzein; H, 2,7,4'-trihydroxyisoflavanone.
Figure 6:
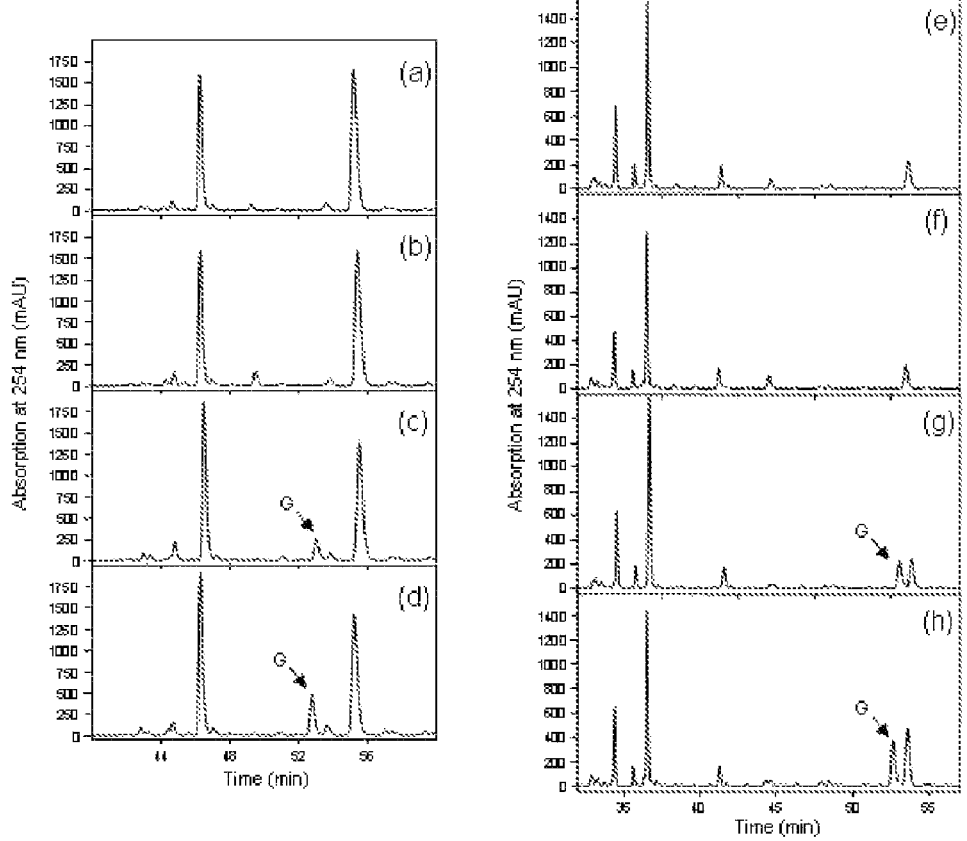
FIG. 6. Production of isoflavones in transgenic tobacco. Traces show HPLC profiles of extracts from petals of transgenic tobacco plants after hydrolysis with 1N HCl (A-D) or β-glucosidase (E-H). Plants were transformed with (A, E) pBI121 vector; (B, F) pBI121-CHI (line 2042-5, see FIG. 10); (C, G) pBI121-IFS (line 2043-10); (D, H) pBI121-IFS/CHI. (line 2044-9). G, genistein.

When liquiritigenin was used as substrate in the absence of NADPH, very low levels of daidzein were observed in microsomes from cells expressing pYeDp60-IFS and pYeDP60-IFS/CHI (FIGS. 5C,D), but not in microsomes expressing empty vector or CHI alone (FIGS. 5A,B). However, when NADPH was included in the reactions, pYeDp60-IFS and pYeDP60-IFS/CHI showed similar levels of conversion of liquiritigenin to daidzein, with the intermediate 2,7,4'-trihydroxyisoflavanone also being detected (FIG. 5 G,H).

Figure 8:
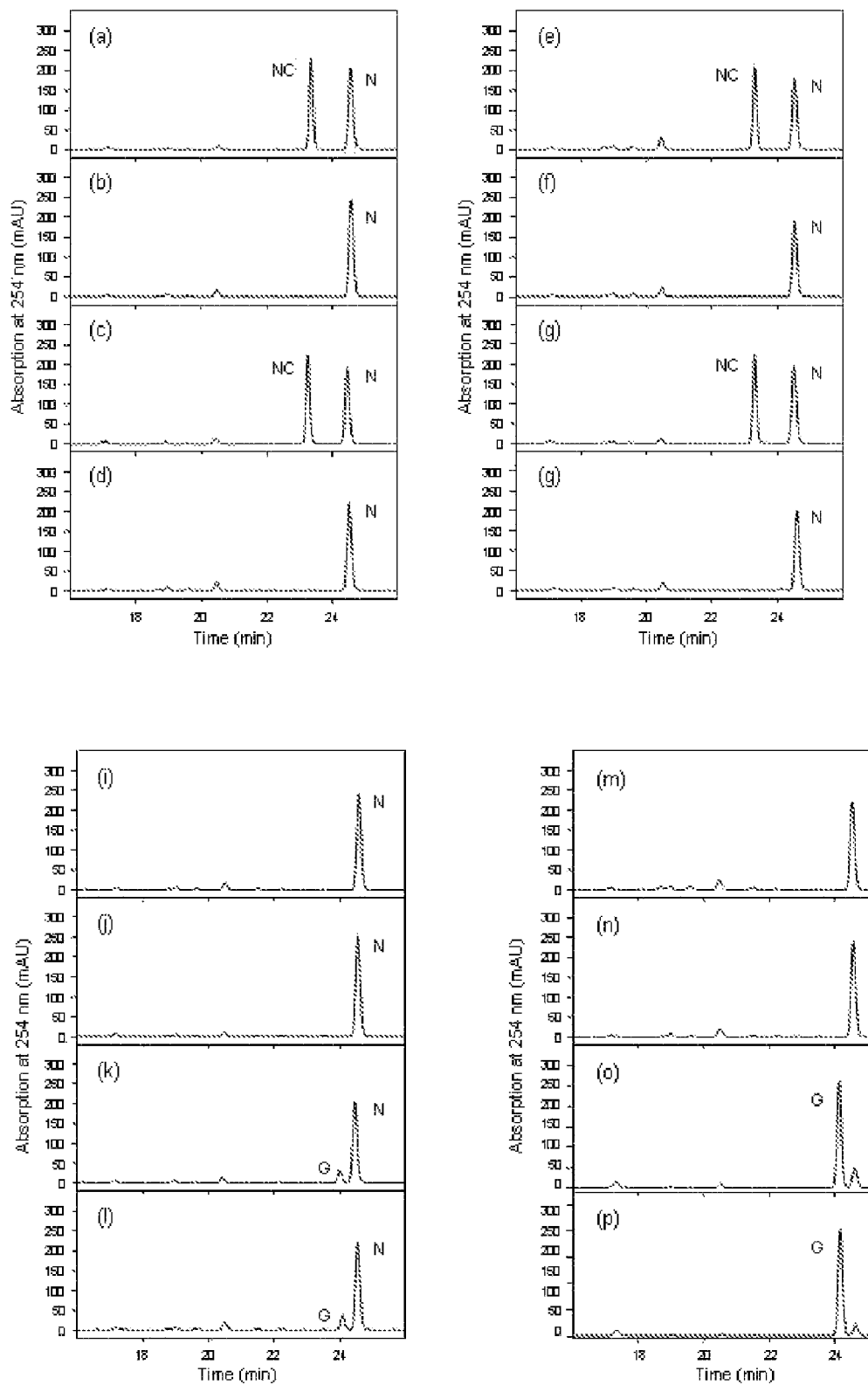
FIG. 8. CHI and coupled CHI/IFS activity of enzymes expressed in yeast (naringenin chalcone as substrate). HPLC elution profiles of in vitro assays with recombinant yeast microsomes expressing pYeDP60 vector (A, E, I, M), alfalfa chalcone isomerase (B, F, J, N), soybean isoflavone synthase (C, G, K, O), and soybean isoflavone synthase-alfalfa chalcone isomerase fusion protein (D, H, L, P). Naringenin chalcone was used as substrate and the reaction mixture was incubated with (E-H, M-P) or without (A-D, I-L) NADPH for 5 min (A-H) or 12 h (1-P). All of the naringenin chalcone isomerized non-enzymatically to naringenin after the 12 h incubation. N, naringenin; G, genistein; NC, naringenin chalcone.
Figure 9:
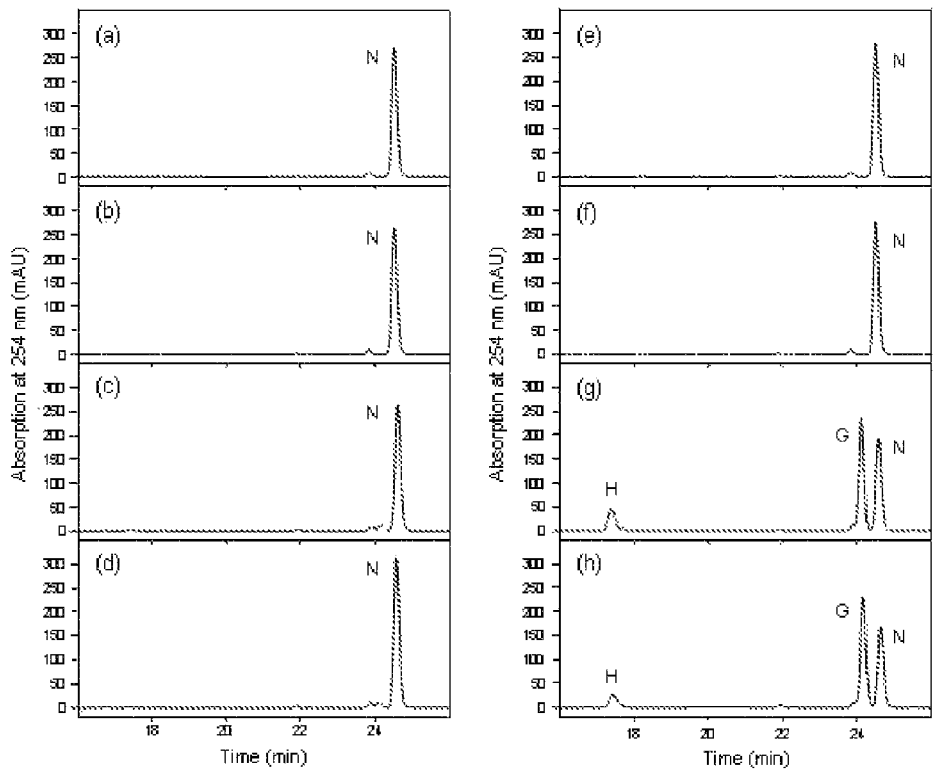
FIG. 9. IFS activity of enzymes expressed in yeast (naringenin as substrate). HPLC elution profiles of in vitro assays with recombinant yeast microsomes expressing pYeDP60 vector (A, E), alfalfa chalcone isomerase (B, F), soybean isoflavone synthase (C, G), and soybean isoflavone synthase-alfalfa chalcone isomerase fusion protein (D, H). Naringenin was used as substrate and the reaction mixture was incubated for 12 h with (E-H) or without (A-D) NADPH. N, naringenin; G, genistein; H, 2,5,7,4'-tetrahydroxyisoflavanone.

Naringenin chalcone and naringenin were also tested as substrates for the enzymes expressed in recombinant yeast microsomes in the presence or absence of NADPH. Activities of the IFS/CHI fusion protein towards these substrates were similar to those observed with isoliquiritigenin and liquiritigenin, respectively (FIGS. 8 and 9).

Example 4

Production of Isoflavones in Transgenic Tobacco Petals and Young Leaves

Figure 10:
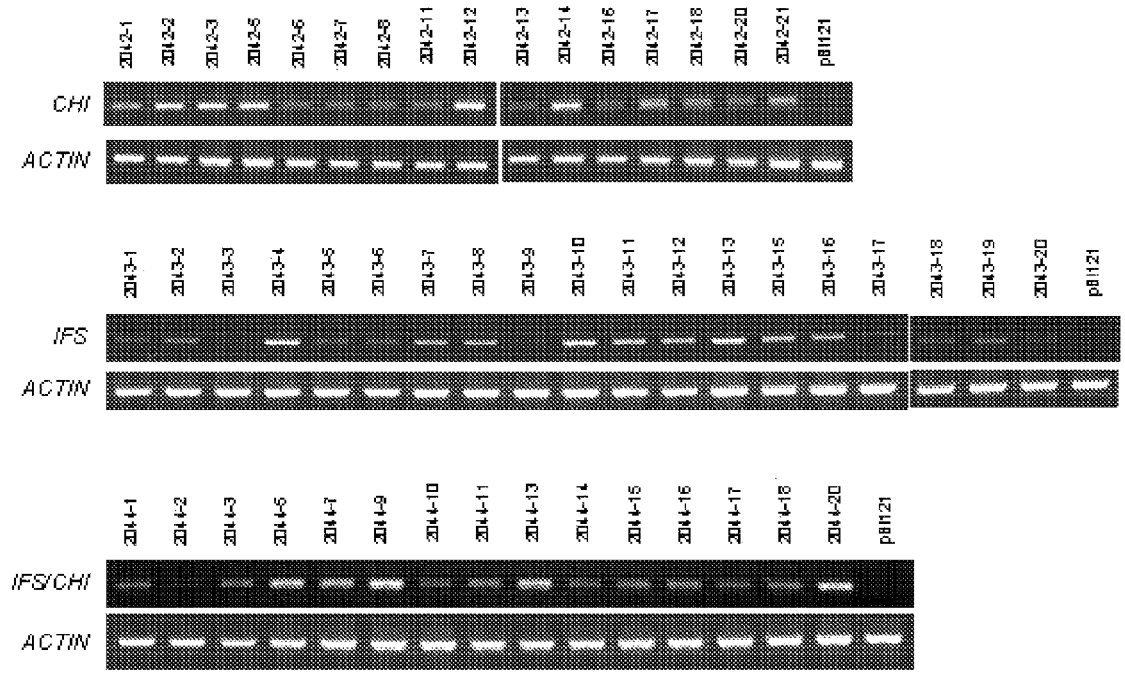
FIG. 10. Levels of CHI, IFS and IFS/CHI transcripts in independent transgenic tobacco lines as determined by semi-quantitative RT-PCR. Actin transcripts were amplified to illustrate equal RNA concentrations in the different extractions.
Figure 11:
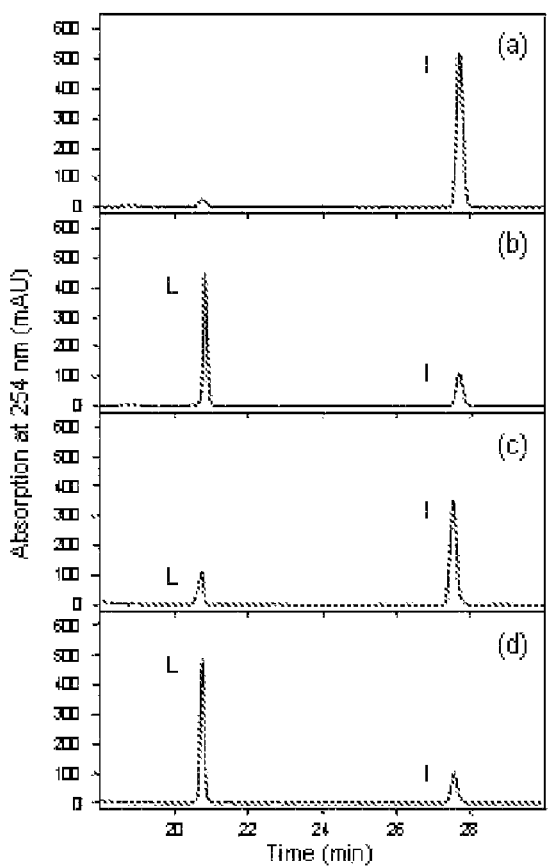
FIG. 11. CHI activity of enzymes expressed in young tobacco leaves. Microsomes were isolated from young leaves of tobacco plants expressing pBI121 vector (A); pBI121-alfalfa CHI (line 2042-5, See FIG. 10) (B); pBI121-soybean IFS (line 2043-10) (C); and pBI121-soybean IFS/alfalfa CHI fusion protein (line 2044-9) (D). Isoliquiritigenin was used as substrate in order to exclude endogenous CHI activity, and the reaction mixtures were incubated without NADPH for 3 h at 16° C. Products were analyzed by HPLC. I, isoliquiritigenin; L, liquiritigenin.

CHI, IFS and IFS/CHI open reading frames were subcloned into the plant transformation vector pBI121. These, and empty vector control construct, were transformed into tobacco (*Nicotiana tabacum* cv Xanthi NN) by *Agrobacterium*-mediated transformation. Transformants were screened for the presence of the transgene by selection for kanamycin resistance and by PCR amplification of the NPTII gene on the pBI121 vector. The expression level of the transgenes was measured by semi-quantitative RT-PCR (FIG. 10), and expression of active protein was confirmed by measuring the CHI activity in microsomal extracts from leaves expressed the alfalfa CHI or the IFS/CHI fusion transgenes using isoliquiritigenin as substrate (FIG. 11). This assay specifically measures the activity of the CHI encoded by the transgenes, since endogenous tobacco CHI cannot use the 6'-deoxy chalcone isoliquiritigenin as substrate. Several independent lines for each construct showed high expression levels of the various transgenes as determined by RT-PCR (FIG. 10), and were further characterized for isoflavone production in leaf and petal tissues.

Figure 12:
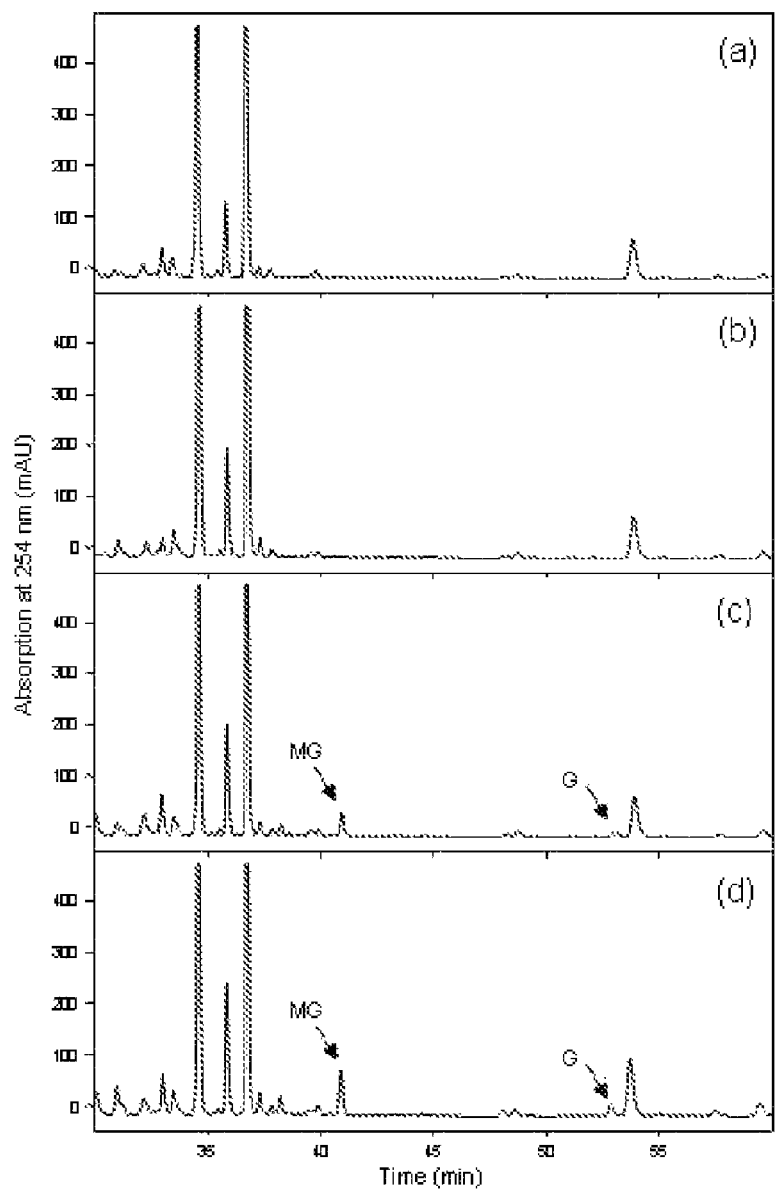
FIG. 12. HPLC profiles illustrating the production of genistein and genistein glycoconjugates in the petals of transgenic tobacco plants. One tenth of the 80% methanol extract was separated on reverse phase HPLC. Plants were transformed with (A) pBI121 vector; (B) pBI121-CHI (line 2042-5); (C) pBI121-IFS (line 2043-10); (D) pBI121-IFS/CHI (line 2044-9). G, genistein; MG, malonyl genistin. Genistin (genistein 7-O-glucoside) comigrates with the peak at 34.583 min.

Total flavonoids from transgenic tobacco petals were extracted with 80% methanol, hydrolyzed with 1 N HCl and separated by reverse phase HPLC (FIG. 6A-D). Genistein was detected in extracts from both IFS and IFS/CHI transgenic plants, but not in extracts from vector control or CHI transgenic plants. Non-hydrolyzed extracts from petals were analyzed by HPLC, and showed the presence of genistein (aglycone), genistin (genistein 7-O-glucoside, which comigrates with the peak at 34.583 min) and malonyl genistin in IFS- and IFS/CHI-expressing plants (FIG. 12). Hydrolysis of the 80% methanol extracts with almond β-glucosidase released genistein from the glucose conjugates (FIG. 6E-F).

Flavonol levels were quantified from petal extracts hydrolyzed in 1N HCl, and genistein from β-glucosidase hydrolyzed samples, by comparison to standard curves (Table 1). Petals from transgenic plants expressing IFS/CHI fusion produced more genistein than petals from plants expressing the IFS transgene alone. The increase in genistein for instance relative to plants expressing the IFS transgene alone was greater than 15%. However, total flavonol levels were not significantly different among the transgenic plants, including empty vector controls (Table 1), indicating that expression of alfalfa CHI does not increase flux into flavonoid biosynthesis in tobacco flowers, and suggesting that the increased production of genistein in IFS/CHI compared to IFS transgenics is most likely the result of improved in vivo efficiency of isoflavone formation from chalcone.

TABLE 1

Genistein and flavonol levels in transgenic tobacco petals[a].

| Plant line[b] | Quercetin nmol/g FW | Kaempferol nmol/g FW | Total flavonols nmol/g FW | Genistein nmol/g FW |
|---|---|---|---|---|
| Control (pBI121 vector) | 2472.89 ± 80.68 | 3549.06 ± 228.09 | 6021.95 ± 155.78 | n.d. |
| 2042-2 (CHI) | 2774.43 ± 76.22 | 3237.16 ± 124.11 | 6011.59 ± 191.60 | n.d. |
| 2042-3 (CHI) | 2760.48 ± 112.52 | 3343.73 ± 92.89 | 6104.21 ± 191.92 | n.d. |
| 2042-5 (CHI) | 2575.40 ± 135.33 | 3626.41 ± 140.38 | 6201.81 ± 182.18 | n.d. |
| 2042-12 (CHI) | 2536.81 ± 218.30 | 3683.25 ± 111.52 | 6220.06 ± 194.85 | n.d. |
| 2042-14 (CHI) | 2671.69 ± 131.19 | 3284.57 ± 108.89 | 5956.27 ± 87.11 | n.d. |
| 2043-4 (IFS) | 3013.30 ± 119.25 | 3081.45 ± 186.81 | 6094.75 ± 140.47 | 225.62 ± 40.92 |
| 2043-10 (IFS) | 3099.63 ± 84.25 | 2929.42 ± 74.36 | 6029.05 ± 148.52 | 235.59 ± 24.36 |
| 2043-12 (IFS) | 3024.22 ± 98.36 | 3129.49 ± 143.53 | 6153.71 ± 65.10 | 174.03 ± 6.32 |
| 2043-13 (IFS) | 2841.16 ± 102.60 | 3127.29 ± 104.85 | 5968.45 ± 196.43 | 190.14 ± 19.78 |
| 2043-15 (IFS) | 3090.13 ± 105.44 | 3017.18 ± 71.68 | 6107.31 ± 112.07 | 161.49 ± 6.31 |
| 2044-5 (IFS/CHI fusion) | 2808.65 ± 63.38 | 3211.31 ± 215.73 | 6019.97 ± 154.45 | 309.57 ± 35.65 |
| 2044-7 (IFS/CHI fusion) | 2911.99 ± 190.63 | 3118.65 ± 184.21 | 6030.63 ± 348.35 | 284.86 ± 31.11 |
| 2044-9 (IFS/CHI fusion) | 2947.96 ± 136.24 | 3176.63 ± 197.89 | 6124.59 ± 168.46 | 415.65 ± 33.01 |
| 2044-13 (IFS/CHI fusion) | 3112.16 ± 106.83 | 3080.86 ± 238.81 | 6193.01 ± 151.25 | 382.39 ± 16.46 |
| 2044-20 (IFS/CHI fusion) | 2848.47 ± 98.33 | 3144.77 ± 109.26 | 5993.24 ± 60.16 | 278.01 ± 23.93 |

Figure 13:
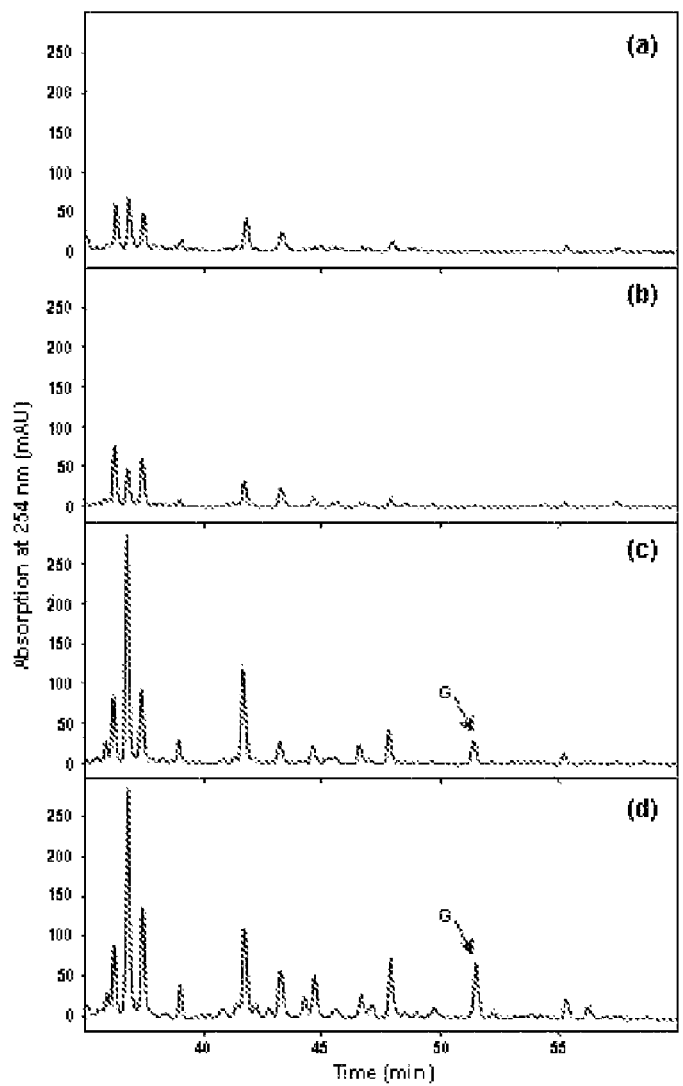
FIG. 13. HPLC profiles of β-glucosidase-hydrolyzed extracts from young transgenic tobacco leaves.

[a]Flavonol levels were calculated from HPLC traces of acid hydrolyzed samples and genistein levels were calculated from HPLC traces of β-glucosidase hydrolyzed samples. Values are for independent transgenic lines as shown, and represent the average and standard deviation from three replicate determinations.
[b]See FIG. 10 for transgene expression data Total flavonoids were also extracted from young transgenic tobacco leaves with 80% methanol, hydrolyzed with β-glucosidase and analyzed by reverse phase HPLC (FIG. 13). Genistein accumulated in both IFS- and IFS/CHI-expressing young leaves, although at a much lower level than in petals (FIG. 13; Table 2). Surprisingly, leaves of IFS- and IFS/CHI-expressing plants accumulated more flavonols, and total UV absorbing compounds, than leaves from vector controls or CHItransgenic plants (FIG. 13; Table 2). As with petals, leaves of plants expressing the IFS/CHI fusion produced more genistein than leaves of plants expressing IFS alone. The increase in genistein for instance relative to plants expressing the IFS transgene alone was at least 20%. Genistein accumulation could not be detected in mature leaves of any of the transgenic plants. Flavonol levels were calculated from acid hydrolyzed samples and genistein levels were calculated from β-glucosidase hydrolyzed samples. Total UV absorbing compounds were measured as described in Yu et al., 2000. Values are for independent transgenic lines as shown, and represent the average and standard deviation from three replicate determinations.

TABLE 2

Levels of genistein, flavonols and total UV absorbing compounds levels in young transgenic tobacco leaves.

| Plant line | Quercetin nmol/g FW | Kaempferol nmol/g FW | Total flavonols nmol/g FW | Total UV absorbing compounds AU/mg FW | Genistein nmol/g FW |
|---|---|---|---|---|---|
| Control (pBI121 vector) | 10.2 ± 0.76 | 8.59 ± 1.35 | 18.81 ± 0.88 | 0.171 ± 0.012 | n.d. |
| 2042-2(CHI) | 16.11 ± 1.19 | 12.71 ± 1.16 | 28.82 ± 1.18 | 0.222 ± 0.018 | n.d. |
| 2042-3 (CHI) | 14.48 ± 0.92 | 13.93 ± 0.78 | 28.41 ± 0.86 | 0.213 ± 0.021 | n.d. |
| 2042-5(CHI) | 16.26 ± 1.55 | 13.11 ± 1.07 | 29.37 ± 1.37 | 0.228 ± 0.012 | n.d. |
| 2042-12 (CHI) | 11.24 ± 0.76 | 16.45 ± 1.67 | 27.69 ± 1.44 | 0.229 ± 0.014 | n.d. |
| 2042-14 (CHI) | 13.13 ± 0.61 | 15.19 ± 1.60 | 28.32 ± 1.27 | 0.231 ± 0.011 | n.d. |
| 2043-4 (IFS) | 53.92 ± 2.77 | 59.58 ± 3.35 | 113.50 ± 3.42 | 0.264 ± 0.009 | 4.48 ± 0.23 |
| 2043-10 (IFS) | 61.65 ± 1.99 | 43.01 ± 3.71 | 104.65 ± 5.64 | 0.258 ± 0.015 | 4.50 ± 0.19 |
| 2043-12 (IFS) | 66.16 ± 4.89 | 50.35 ± 3.63 | 116.51 ± 3.78 | 0.266 ± 0.015 | 4.01 ± 0.55 |
| 2043-13 (IFS) | 58.31 ± 0.47 | 45.14 ± 1.79 | 103.46 ± 1.33 | 0.267 ± 0.013 | 4.32 ± 0.40 |
| 2043-15 (IFS) | 60.07 ± 1.43 | 47.99 ± 2.34 | 108.06 ± 1.91 | 0.258 ± 0.011 | 3.89 ± 0.24 |
| 2044-5 (IFS/CHI fusion) | 68.46 ± 7.84 | 73.57 ± 6.76 | 142.03 ± 7.11 | 0.261 ± 0.014 | 6.16 ± 0.76 |
| 2044-7 (IFS/CHI fusion) | 78.01 ± 5.34 | 80.22 ± 4.82 | 158.23 ± 5.10 | 0.268 ± 0.014 | 5.62 ± 0.44 |
| 2044-9 (IFS/CHI fusion) | 80.59 ± 4.95 | 87.25 ± 5.47 | 167.84 ± 6.46 | 0.264 ± 0.017 | 8.21 ± 0.68 |
| 2044-13 (IFS/CHI fusion) | 89.88 ± 7.46 | 60.32 ± 5.29 | 150.20 ± 5.11 | 0.262 ± 0.021 | 7.43 ± 0.51 |
| 2044-20 (IFS/CHI fusion) | 81.51 ± 4.13 | 68.40 ± 4.99 | 149.91 ± 4.72 | 0.272 ± 0.018 | 5.45 ± 0.37 |

Example 5

Rational Design of a Bifunctional Fusion Protein as Directed by the Structural/Functional Properties of the Components A primary consideration for protein engineering is the targeted delivery of the recombinant protein to the functional compartment where its substrates and/or co-enzymes are accessible (Ptashne and Gann, 2002). Although CHI/IFS and IFS/CHI fusions would be functionally equivalent in vitro, IFS protein is preferably at the N-terminus (i.e. IFS/CHI) to guide the fusion protein to the outer (cytosolic) face of the ER membrane, where its co-acting enzyme, NADPH-cytochrome P450 reductase, is located. The transient expression study in tobacco leaf epidermal cells confirmed that the IFS/CHI fusion protein localized correctly to the ER.

A key factor in generating a fusion protein is maintaining the functionality of the individual components. A direct head to tail fusion of two proteins together often restrains the correct folding of the individual components, and hence leads to non-functional or mal-functional enzymes (Netzer and Hartl, 1997). The availability of three dimensional structures of IFS (modeled, based on Williams et al., 2000) and CHI (experimentally determined) (Jez et al., 2000) facilitated the design of the fusion protein. Molecular modeling of the IFS/CHI fusion indicated a flexible linkage between the two proteins, and a three-amino-acid linker of glycine and serine residues was added to confer additional flexibility to the linkage without interfering with function. The flexible linkage between the protein components enables them to interact with their ligands in a dynamic environment.

The relative spatial orientations of the active sites were also considered when designing the fusion protein. The substrate binding site of CHI locates at the bottom of the upside-down bouquet structure and consists of the residues from β-strands β3a and β3b and α-helices α4 and α6 (FIG. 2C) (Jez et al., 2000). Previous site-directed mutagenesis of the IFS (CYP93C2) protein defined the substrate binding pocket as involving predicted helix I and β-sheet 1-4 (Sawada et al., 2002). Based on the 3-D model of the IFS/CHI fusion protein, the active sites of the two enzymes are well-exposed to catalyze sequential reactions (FIGS. 2B, C). When the recombinant IFS/CHI fusion protein was expressed in yeast, the refolded protein was able to catalyze conversion of chalcones to their corresponding isoflavone derivatives, indicating that the fusion protein retained the function of the component modules.

Example 6

The Isoflavonoid Biosynthetic Pathway Introduced into Non-Legume Plants Expressing the IFS/CHI Gene Fusion Expression of the IFS/CHI fusion protein established the early steps of the isoflavonoid biosynthetic pathway in a non-legume plant, tobacco, resulting in the accumulation of genistein and genistein glycosides in petal and young leave tissues. Tobacco flowers naturally accumulate pink anthocyanin pigments, consisting mainly of conjugates of cyanidin (Xie et al., 2003). Because anthocyanins use the same precursors as isoflavonoid biosynthesis (Winkel-Shirley, 2001), tobacco flowers contain the necessary chalcone and flavonoid substrate pools for the engineered isoflavone accumulation.

Tobacco plants expressing the IFS transgene alone accumulated genistein and genistein glycosides in both petals and young leaves, although at lower levels than in plants expressing the IFS/CHI fusion. In *Arabidopsis*, genistein accumulation in leaf tissue was not further increased by introducing CHI into IFS-expressing transgenic plants (Liu et al., 2002). It was suggested that competition between the endogenous flavonoid pathway and the introduced isoflavonoid pathway was the limiting step for isoflavonoid production in transgenic *Arabidopsis*. In the present study, expression of the IFS/CHI fusion clearly increased the production of genistein glycosides in tobacco compared to expression of the IFS transgene alone. One possible reason for this was that the IFS enzyme in the IFS/CHI fusion was more efficient in vivo because the flavanone substrate for IFS (the product of CHI) was more readily available in the fusion protein, i.e. the distance that the flavanone has to diffuse to the IFS active site is drastically reduced. The observed differences between *Arabidopsis* and tobacco may also be due to the different flavonoid compositions, and therefore potentially different competing pathways, in the two plants, although both species produce glycosylated flavonols as major components of the leaf phenolic profile.

To more rigorously test whether the apparently improved efficiency of isoflavone production in plants expressing IFS/CHI is indeed the result of kinetic factors, it may be desired to compare metabolite production in plants expressing similar levels of IFS and CHI as single enzymes or as fusion protein. It may also be important to determine whether the flavonol pathway competes with IFS for naringenin substrate in tobacco petals and leaves. To this end, IFS- and CHI-expressing transgenic plants may be crossed to provide material in which both components of the IFS/CHI fusion are expressed but as single enzymes, and the IFS/CHI fusion may be introduced into plants expressing an antisense construct targeting flavanone 3-hydroxylase (F3H), to block the competing endogenous flavonol pathway.

Free genistein was detected in extracts from young tobacco leaves expressing IFS and IFS/CHI fusion transgenes, but only after hydrolysis with β-glucosidase. A previous analysis of IFS transgenic tobacco plants could not detect free genistein in leaves (Yu et al., 2000). Genistein was not detected in mature transgenic tobacco leaves after hydrolysis, suggesting that production and turnover of genistein aglycone and glycosides are developmentally regulated.

Daidzein is, along with genistein, a major soy phytoestrogen (Dixon, 2004) and precursor for a range of antimicrobial isoflavonoids in the Leguminosae (Dixon, 2001), and is used, as its 7-O-glucoside, as a treatment for alcoholism (Keung and Vallee, 1993). The endogenous CHI found in tobacco is not active with isoliquiritigenin, the precursor of 5-deoxyisoflavonoids such as daidzein, which are produced via a distinct form of CHI exemplified by the legume CHI utilized in the present work (Shimada et al., 2003). The additional activity of *Medicago* CHI with isoliquiritigenin, yielding liquiritigenin as a substrate for IFS, should allow for daidzein production in the present plants expressing IFS/CHI. To achieve this, the plants may be further transformed to express chalcone reductase, an enzyme which acts on the near end-product of the chalcone synthase reaction to produce the corresponding 6'-deoxychalcone isoliquiritigenin (FIG. 1; Bomati et al., 2005), instead of the product naringenin chalcone formed in the absence of the chalcone reductase.

Example 7

Metabolic Engineering of Membrane-Bound Cytochrome P450 Proteins

Cytochrome P450s are a large group of enzymes common to animals and plants. Cytochrome P450 enzymes are targeted to various subcellular localizations, such as ER, chloroplast, mitochondria and plasma membranes (Werck-Reichhart et al., 2002). The present fusion protein approach takes advantage of the subcellular targeting sequence of the cytochrome P450 enzyme, IFS, and adds an additional enzymatic function to it without altering its native activity. In principle, the membrane-targeting sequences of cytochrome P450 enzymes could be used as anchors for hybrid enzymes. Potential examples include fusions between cytochrome P450s and glycosyltransferases, which often glucosylate aromatic hydroxyl groups, introduced by P450 enzymes, to facilitate storage or increase/decrease bioactivity of plant natural products. Plant small molecule glycosyltransferases are operationally soluble enzymes (Vogt and Jones, 2000), but may be associated with P450 enzymes, for example in the cyanogenic glucoside pathway that utilizes CYP79A1 and CYP71E1 (Jorgensen et al., 2005). Although the components of the cyanogenic glycoside pathway have been engineered into plants as single, independent constructs (Tattersall et al., 2001), it has not previously been determined whether a fusion enzyme approach would facilitate engineering of this or related pathways.

On the other hand, cytochrome P450 enzymes may be engineered to have alternative subcellular localizations, which may lead to availability of diverse, novel substrates and therefore potential novel functions for these enzymes. The knowledge gained from engineering cytochrome P450 enzymes can be further applied to other membrane-bound proteins, some of which are targets for medicinal drugs and have potential use in biotechnology. One outstanding example is the development of artificial receptor proteins that combine the ligand-binding region of receptors with carrier proteins of favorable scaffolds (Skerra, 2003). Such proteins imitate the action of immunoglobulins and have found value in both basic research and pharmaceutical applications (Hey et al., 2005).

Example 8

Materials and Methods

A. Chemicals and Plant Materials

Isoliquiritigenin, liquiritigenin, naringenin and genistein were purchased from Indofine Chemical Co. (Hillsborough, N.J.). Naringenin chalcone was prepared from naringenin as previously described (Shimokoriyama, 1957).

*Nicotiana tabacum* cv Xanthi NN plants were grown in soil at 64-93 $\mu mol.m^{-2}.s^{-1}$ under an 18 h-light/6 h-dark cycle (24° C. and 50%-75% humidity) in the greenhouse. Young leaves were used for transient expression studies and as starting material for tobacco transformation. Transgenic tobacco plants were grown in the greenhouse under the above described conditions. Petal tissue and young leaves were collected for total flavonoid analysis.

B. Plasmid Constructs for Yeast Transformation, Plant Transformation and Transient Expression in Tobacco Sequences of the primers used for subcloning are listed in Table 3. All of the Polymerase Chain Reaction (PCR) reactions were performed using high-fidelity Pfu DNA polymerase (Stratagene, La Jolla, Calif.). The PCR amplified regions in all constructs were sequenced to ensure that no mutations were introduced during subcloning.

For construction of the IFS/CHI fusion enzyme for expression in yeast, the soybean IFS open reading frame was amplified from the plasmid carrying soybean IFS2 (GenBank accession number AF135484; Steele et al., 1999) with primers containing KpnI (5' end) and BamHI (3'-end) sites (Table 3), and inserted into the KpnI and BamHI sites of pBlueScript KS+vector. A 650 bp fragment containing the alfalfa CHI open reading frame was amplified from the plasmid carrying alfalfa CHI (GenBank accession number M91079; Liu et al., 2002) with primers containing a BamHI site and a Gly-Ser-Gly linker sequence, GGATCCGGA, at the 5'-end, and a SacI site at the 3'-end (Table 3). PCR products were digested with BamHI and SacI and ligated to pBlueScript KS+-IFS predigested with BamHI and SacI. The resulting IFS/CHI fusion fragment was inserted into the KpnI and SacI sites of the yeast pYeDP60 vector. Soybean IFS and alfalfa CHI open reading frames were also subcloned into the pYeDP60 vector singly and used as controls in the yeast expression studies.

For plant transformation, the β-glucuronidase coding region was removed from the binary vector pBI121 (Clontech, Mountain View, Calif.) and replaced by the coding regions of CHI, IFS, or IFS/CHI fusion, respectively. Primers used for constructing plant transformation plasmids are listed in Table 3. Gene expression was under control of the cauliflower mosaic virus 35S promoter and nos terminator.

For construction of a chimeric IFS/CHI/Enhanced Green Fluorescent Protein (EGFP; Clontech, Palo Alto, Calif.) gene, the following two-step recombinant PCR strategy was applied (Higuchi, 1990). In the first step, the IFS/CHI fusion open reading frame was amplified using pBluescript KS+-IFS/CHI fusion as a template, with a forward primer to introduce an XhoI restriction site and a reverse primer containing reverse complementary sequences from the end of CHI and the start of the EGFP open reading frames. Similarly, EGFP was amplified using a forward primer with reverse complementarity to CHI and a reverse primer with an introduced XbaI restriction site. The resulting IFS/CHI and EGFP open reading frame fragments were recovered from an agarose gel and served as templates in a second PCR reaction using the IFS forward (with an XhoI site) and EGFP reverse (with an XbaI site) primers. After digestion with XhoI and XbaI, the resulting chimeric cDNA was inserted into the corresponding sites of the shuttle vector pRTL2 (Restrepo et al., 1990) under the control of a double 35S promoter. The DNA fragment encoding free EGFP was amplified with a forward primer containing an XhoI restriction site and the EGFP reverse primer (with an XbaI site) and was also inserted in pRTL2. A pRTL2-C4H MA-EGFP construct (Achnine et al., 2004) was used as a positive control for ER-membrane localization.

TABLE 3

Sequences of primers used for subcloning.

| Experiment | Construct | Template | Primer sequence | Restriction site |
|---|---|---|---|---|
| Yeast expression | IFS/CHI fusion | Soybean IFS | 5'-ATGGTACCATGTTGCTTGAACTTGCA-3' (SEQ ID NO: 1) | Kpn I |
| Yeast expression | IFS/CHI fusion | Soybean IFS | 5'-TAGGATCCAGAAAGGAGTTTAGATGCA-3' (SEQ ID NO: 2) | BamH I |

TABLE 3-continued

Sequences of primers used for subcloning.

| Experiment | Construct | Template | Primer sequence | Restriction site |
|---|---|---|---|---|
| Yeast expression | IFS/CHI fusion | Alfalfa CHI | 5'-ATGGATCCGGAATGGCTGCATCAATC-3' (SEQ ID NO: 3) | BamH I |
| Yeast expression | IFS/CHI fusion | Alfalfa CHI | 5'-TAGAGCTCTCAGTTTCCAATCTTGAA-3' (SEQ ID NO: 4) | Sac I |
| Yeast expression | IFS | Soybean IFS | 5'-ATGGTACCATGTTGCTTGAACTTGCA-3' (SEQ ID NO: 1) | Kpn I |
| Yeast expression | IFS | Soybean IFS | 5'-TAGAGCTCTTAAGAAAGGAGTTTAG-3' (SEQ ID NO: 5) | Sac I |
| Yeast expression | CHI | Alfalfa CHI | 5'-ATGGTACCATGGCTGCATCAATC-3' (SEQ ID NO: 6) | Kpn I |
| Yeast expression | CHI | Alfalfa CHI | 5'-TAGAGCTCTCAGTTTCCAATCTTGAA-3' (SEQ ID NO: 4) | Sac I |
| Plant transformation | IFS/CHI fusion | IFS/CHI fusion | 5'-ATTCTAGAATGTTGCTTGAACTTGCA-3' (SEQ ID NO: 7) | Xba I |
| Yeast expression | IFS/CHI fusion | Soybean IFS | 5'-TAGGATCCAGAAAGGAGTTTAGATGCA-3' (SEQ ID NO: 2) | BamH I |
| Yeast expression | IFS/CHI fusion | Alfalfa CHI | 5'-ATGGATCCGGAATGGCTGCATCAATC-3' (SEQ ID NO: 3) | BamH I |
| Yeast expression | IFS/CHI fusion | Alfalfa CHI | 5'-TAGAGCTCTCAGTTTCCAATCTTGAA-3' (SEQ ID NO: 4) | Sac I |
| Plant transformation | IFS | Soybean IFS | 5'-ATTCTAGAATGTTGCTTGAACTTGCA-3' (SEQ ID NO: 7) | Xba I |
| Plant transformation | CHI | Alfalfa CHI | 5'-ATTCTAGAATGGCTGCATCAATC-3' (SEQ ID NO: 8) | Xba I |
| Transient expression | IFS/CHI fusion | IFS/CHI fusion | 5'-ATCTCGAGATGTTGCTTGAACTTGCA-3' (SEQ ID NO: 9) | Xho I |
| Transient expression | IFS/CHI fusion | IFS/CHI fusion | 5'-GCCCTTGCTCACCAT/GTTTCCAATCTTGAA-3' (SEQ ID NO: 10) | — |
| Transient expression | IFS/CHI fusion | EGFP | 5'-TTCAAGATTGGAAAC/ATGGTGAGCAAGGGC-3' (SEQ ID NO: 11) | — |
| Transient expression | IFS/CHI fusion | EGFP | 5'-AGTTATCTAGAGTCGCGGCC-3' (SEQ ID NO: 12) | Xba I |
| Transient expression | EGFP | EGFP | 5'-ATCTCGAGATGGTGAGCAAGGGC-3' (SEQ ID NO: 13) | Xho I |

C. Transient Expression Assay and Confocal Microscopy

Plasmid DNAs (5 μg) harboring EGFP, C4H-MA-EGFP, or IFS/CHI-EGFP, under the control of the double 35S promoter, were transiently expressed in young tobacco leaf epidermal cells as previously described (Liu and Dixon, 2001). Briefly, plasmid DNA coated gold particles were fired at 900 p.s.i., and tobacco leaves were examined 12 h after bombardment using a Bio-Rad 1024ES confocal imaging system. Confocal images were collected and assembled using Adobe Photoshop 5.0 L.E. (Adobe Systems, San Jose, Calif.).

D. Expression and Assay of Recombinant Proteins in Yeast

Transformation of yeast WAT11 cells with the empty pYeDP60 vector and pYeDP60-CHI, pYeDP60-IFS, or pYeDP60-IFS/CHI fusion constructs and preparation of microsomes were conducted as previously described (Liu et al., 2003). Microsomal protein concentrations were determined by the Bradford assay (Bradford, 1976).

Isoliquiritigenin, liquiritigenin, naringenin chalcone or naringenin (8 μM) were incubated with 0.8 mg of recombinant yeast microsomes in the presence or absence of 1 mM NADPH. The reaction mixture was incubated at 16° C. for 12 h and extracted twice with an equal volume of ethyl acetate. The ethyl acetate fractions were pooled, dried under $N_2$, resuspended in methanol and analyzed by reverse phase HPLC using the gradient described in Akashi et al., 1999. The identity of the peaks was confirmed by the retention times and by comparison with authentic standards.

E. Plant Transformation and Molecular Characterization of Transgenic Tobacco Plants Binary vector constructs were transformed into *Agrobacterium tumefaciens* strain LBA4404 by electroporation. Transformed *Agrobacteria* were confirmed by colony PCR, and the constructs transformed into *Nicotiana tabacum* cv Xanthi NN leaf discs as previously described (Horsch et al., 1988). T1 transformants were selected on MS media containing kanamycin, and the kanamycin resistant plantlets were transferred to soil after 14 days.

Genomic DNA was extracted from transgenic tobacco plants using a DNeasy Plant mini kit (Qiagen, Valencia, Calif.). The presence of the transgene was confirmed by amplification with NPTII primers and the PCR products were subjected to 1% agarose gel electrophoresis.

Transgene expression in leaf tissue was determined by semi-quantitative RT-PCR. Total RNA was extracted from young transgenic tobacco leaf tissue with TRI reagent (Molecular Research Center, Inc., Cincinnati, Ohio) and treated with RQ1 RNase-free DNase (Promega, Madison, Wis.) following the manufacturer's instructions. Two µg of total RNA was used as template for first-strand cDNA synthesis with an oligo-dT(16) primer using RT-beads (Amersham Pharmacia Biotech, Piscataway, N.J.). Primers used for second strand cDNA synthesis are listed in Table 4. Linearity of the PCR reaction was monitored by comparing relative amounts of PCR products after 22, 24, 26 and 30 cycles. The optimized PCR cycling conditions were as follows: 94° C. for 3 min, 24 cycles of 94° C. for 30 sec, 55° C. for 30 sec, 72° C. for 2 min, and 1 cycle of 72° C. for 10 min.

TABLE 4

Sequences of primers used for 2nd strand cDNA synthesis.

| Transcript | Forward primer | Reverse Primer |
|---|---|---|
| Actin | 5'-GATATGGAAAAGATCT GGCATCAC-3' (SEQ ID NO: 14) | 5'-TCATACTCGGCCTTGG AGATCCAC-3' (SEQ ID NO: 17) |
| Alfalfa CHI | 5'-GCTGCATCAATCACCG CAATCA-3' (SEQ ID NO: 15) | 5'-GTTTCCAATCTTGAAA GCAC-3' (SEQ ID NO: 18) |
| Soybean IFS | 5'-ATTCTAGAATGTTGCT TGAACTTGCA-3' (SEQ ID NO: 7) | 5'-TAGAGCTCTTAAGAAA GGAGTTTAG-3' (SEQ ID NO: 5) |
| IFS/CHI fusion | 5'-GGCTACTTCGGGAATG GCAACAC-3' (SEQ ID NO: 16) | 5'-TAAAAGTCAAGGGTCT CAAGTAAC-3' (SEQ ID NO: 19) |

F. HPLC Analysis of Total Flavonoids in Transgenic Tobacco Plants

Transgenic tobacco petals and young leaves were ground to a fine power in liquid $N_2$. Tissue (0.1 g) was extracted with 2 ml 80% methanol overnight at 4° C. The extract was centrifuged to remove tissue debris and the supernatant dried under a stream of $N_2$. For β-glucosidase hydrolysis, 3 ml of 5 mg/ml β-glucosidase in citric acid buffer (pH 5.5) was added to the dried samples and the reaction was incubated at 37° C. for 12 h and extracted twice with 3 ml ethyl acetate. For acid hydrolysis, the dried samples were incubated with 3 ml of 1N HCl at 90° C. for 2 h and extracted twice with 3 ml of ethyl acetate. For both β-glucosidase and acid hydrolyses, the ethyl acetate extracts were pooled and dried under $N_2$ and resuspended in 100 µl methanol. Ten µl of the methanolic solution was used for HPLC analysis.

The separation of hydrolyzed and non-hydrolyzed leaf extracts was carried out by reverse-phase HPLC as previously described (Achnine et al., 2005). The separation of petal flavonoids was performed using the following modified gradient: solvent A (1% phosphoric acid) and B (acetonitrile) at 1 ml/min flow rate: 0-5 min, 5% B; 5-10 min, 5% to 10% B; 10-25 min, 10% to 17% B; 25-30 min, 17% to 23% B; 30-39 min, 23% to 30% B; 39-59 min, 30% to 35% B; 59-85 min, 35% to 50% B; 89-99 min, 50%-100% B; 99-100 min, 100% to 5% B. Data were collected at 254, 270, 280, 315 and 524 nm.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 5,302,523
U.S. Pat. No. 5,322,783
U.S. Pat. No. 5,384,253
U.S. Pat. No. 5,464,765
U.S. Pat. No. 5,508,184
U.S. Pat. No. 5,508,468
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042
Aarts et al., *Plant Cell*, 7, 2115-2127, 1995.
Abdullah et al., *Biotechnology*, 4:1087, 1986.
Achnine et al., *Plant Cell*, 16:3098-3109, 2004.
Achnine et al., *Plant J.*, 41:875-887, 2005.
Aharoni et al., *Plant Cell*, 16: 2463-2480, 2004.
Akashi et al., *Plant Physiol.*, 121:821-828, 1999.
Akashi et al., *Plant Physiol.*, 137:882-891, 2005.
Austin et al., *Euphytica*, 85, 381-393, 195.
Barnes, *J. Nutr.*, 134:1225 S-1228S, 2004.
Bateman et al., *Nucl. Acids. Res.*, 30, 276-280, 2002.
Bates, *Mol. Biotechnol.*, 2(2):135-145, 1994.
Battraw and Hall, *Theor. App. Genet.*, 82(2):161-168, 1991.
Bednar and Hadcock, *J. Biol. Chem.*, 263:9582-9588, 1988.
Bergman et al., *Environ. Entomol.*, 20,781-785, 1991.
Bevan et al., *Nucleic Acids Research*, 11(2):369-385, 1983.
Bhattacharajee et al., *J. Plant Bioch. and Biotech.* 6, (2):69-73. 1997.
Bomati et al., *J. Biol. Chem.*, 280:30496-30503, 2005.
Bower et al., *Plant J.*, 2:409-416. 1992.
Bradford, *Anal Biochem.*, 72:248-254, 1976.
Broun et al., *Proc. Natl. Acad. Sci. USA*, 101:4706-4711, 2004.
Buchanan-Wollaston et al., *Plant Cell Reports*, 11:627-631, 1992
Buising and Benbow, *Mol Gen Genet*, 243(1):71-81, 1994.
Bülow, *Biochem. Soc. Symp.*, 57:123-133, 1990.

Callis et al., *Genes Dev.*, 1:1183-1200, 1987.
Casa et al., *Proc. Natl. Acad. Sci. USA*, 90(23):11212-11216, 1993.
Chakravarthy et al., *Plant Cell*, 15:3033-3050, 2003.
Chandler et al., *Plant Cell*, 1: 1175-1183, 1989.
Chen et al., *Plant Cell*, 15, 1170-1185, 2003.
Christou; et al., *Proc. Natl. Acad. Sci. USA*, 84(12):3962-3966, 1987.
Chu et al., *Scientia Sinica*, 18:659-668, 1975.
Conkling et al., *Plant Physiol.*, 93:1203-1211, 1990.
Cornwell et al., *Phytochemistry*, 65:995-1016, 2004.
D'Halluin et al., *Plant Cell*, 4(12):1495-1505, 1992.
DE 3642 829 A
De Block et al., *EMBO J.*, 6(9):2513-2518, 1987.
De Block et al., *Plant Physiol.*, 91:694-701, 1989.
DellaPenna, *Science*, 285:375-379, 1999.
Dellaporta et al., In: *Chromosome Structure and Function: Impact of New Concepts*, 18th Stadler Genetics Symposium, 11:263-282, 1988.
Dixon and Ferreira, *Phytochemistry*, 60:205-211, 2002.
Dixon, *Annu. Rev. Plant Biol.*, 55:225-261, 2004.
Dixon, *Curr. Opin. Plant Biol.*, 8:329-336, 2005.
Dixon, *Nature*, 411:843-847, 2001.
Dubouzet et al., *Plant J.*, 33, 751-763, 2003.
Ebert et al., *Proc. Natl. Acad. Sci. USA*, 84:5745-5749, 1987.
European Patent Application 154, 204
Fahrendorf and Dixon, *Arch. Biochem. Biophys.* 305, 509-515, 1993.
Fiebig et al., *Plant Cell*, 12:2001-2008, 2000.
Fraley et al., *Bio/Technology*, 3:629-635, 1985.
Fromm et al., *Nature*, 319:791-793, 1986.
Galili and Hofgen, *Metab. Eng.*, 4:3-11, 2002.
Gallie et al., *Plant Cell*, 1:301-311, 1989.
Gelvin et al., In: *Plant Molecular Biology Manual*, 1990.
Ghosh-Biswas et al., *J. Biotechnol.*, 32(1):1-10, 1994.
Gilmour et al., *Plant Physiol.*, 124, 1854-1865, 2000.
Gowri et al., *Plant Physiol.* 97, 7-14, 1991
Gutterson and Reuber, *Curr. Opin. Plant Biol.*, 7, 465-471, 2004.
Haake et al., *Plant Physiol.*, 130, 639-648, 2002.
Hagio et al., *Plant Cell Rep.*, 10(5):260-264, 1991.
Hamilton et al., *Proc. Natl. Acad. Sci. USA*, 93(18):9975-9979, 1996.
Hannoufa et al., *Plant J*, 10, 459-467, 1996.
Hansen et al., *Plant Physiol.*, 113, 1091-1100, 1997.
Haseloff et al., *Proc. Natl. Acad. Sci. USA*, 94(6):2122-2127, 1997.
He et al., *Plant Cell Reports*, 14 (2-3):192-196, 1994.
Hensgens et al., *Plant Mol. Biol.*, 22(6):1101-1127, 1993.
Hey et al., *Trends Biotech.*, 23(10):514-522, 2005.
Hiei et al., *Plant. Mol. Biol.*, 35(1-2):205-218, 1997.
Higuchi, In: *PCR Protocols*, Innis et al. (Eds.), NY, Academic Press, 177-182, 1990.
Hinchee et al., *Bio/technol.*, 6:915-922, 1988.
Hoffmann et al., *J. Biol. Chem.* 278, 95-103, 2003.
Hooker et al., *Plant Physiol.*, 129, 1568-1580, 2002.
Horsch et al., In *Plant Molecular Biology Manual*, Gelvin and Schilperoort (Eds.), Dordrecht: Kluwer Academic Publishers, A5: 1-9, 1988.
Hou and Lin, Plant Physiology, 111:166, 1996.
Hudspeth and Grula, Plant Mol. Biol., 12:579-589, 1989.
Ikuta et al., *Bio/technol.*, 8:241-242, 1990.
Ishidia et al., *Nat. Biotechnol.*, 14(6):745-750, 1996.
Jaglo-Ottosen et al., Science, 280, 104-106, 1998.
James and Viola, *Biochemistry*, 41:3726-3731, 2002.
Jefferson, *Crop Sci.*, 34, 367-371, 1994.
Jenks and Ashworth, In: *Horticultural Reviews*, Janick (Ed.), 1-68. John Wiley & Sons, Inc., NY, 1999.
Jenks et al., *Plant Physiol.*, 108:369-377, 1995.
Jenks In: The *Arabidopsis Book*, Somerville and Meyerowitz (Eds.), American Society of Plant Biologists, Rockville, Md., 2002.
Jez et al., *Nat. Struct. Biol.*, 7:786-791, 2000.
Jofuku et al., *Plant Cell*, 6:1211-1225, 1994.
Jorgensen et al., *Curr. Opinion Plant Biol* 8, 280-291, 2005.
Jorgensen et al., *Plant Physiol.* 139(1):363-374, 2005.
Kaeppler et al., *Plant Cell Reports*, 9:415-418, 1990.
Kaeppler et al., *Theor. Appl. Genet.*, 84(5-6):560-566, 1992.
Kasuga et al., *Nat. Biotechnol.*, 17:287-291, 1999.
Kasuga et al., *Plant Cell Physiol.*, 45, 346-350, 2004.
Katz et al., *J. Gen. Microbiol.*, 129:2703-2714, 1983.
Kerstiens, *Trends Plant Sci.*, 1, 125-129, 1996.
Keung and Vallee, *Proc. Natl. Acad. Sci. USA*, 90:1247-1251, 1993.
Klee et al., *Bio-Technology*, 3(7):637-642, 1985.
Knittel et al., *Plant Cell Reports*, 14(2-3):81-86, 1994.
Kochs and Grisebach, *Eur. J. Biochem.*, 155:311-318, 1986.
Koomneef et al., *J. Hered.*, 80, 118-122, 1989.
Kourtz et al., *Plant Biotech J* 3:435-447, 2005.
Kunst and Samuels, *Prog. Lipid Res.*, 42, 51-80, 2003.
La Camera et al., *Immunol. Rev.*, 198:267-284, 2004.
Lawton et al., *Plant Mol. Biol.* 9:315-324, 1987.
Lazzeri, *Methods Mol. Biol.*, 49:95-106, 1995.
Lee et al., *Korean J. Genet.*, 11(2):65-72, 1989.
Li et al., *Proc. Natl. Acad. Sci. USA*, 100:4939-4944, 2003.
Lin et al., *Proc. Natl. Acad. Sci. USA*, 100:5962-5967, 2003.
Liu and Dixon, *Plant Cell*, 13:2643-2658, 2001.
Liu et al., *Plant Cell*, 10, 1391-1406, 1998.
Liu et al., *Plant J.* 36, 471-484, 2003.
Liu et al., *Plant J.*, 36:471-484, 2003.
Liu et al., *Proc. Natl Acad. Sci. USA*, 99:14578-14583, 2002.
Lolle et al., *Dev. Biol.*, 189, 311-321, 1997.
Lorz et al., *Mol Gen Genet*, 199:178-182, 1985.
Marcotte et al., *Nature*, 335:454, 1988.
McCabe and Martinell, *Bio-Technology*, 11(5):596-598, 1993.
McCormac et al., *Euphytica*, 99(1):17-25, 1998.
Millar et al., *Plant Cell*, 11, 825-838, 1999.
Moose and Sisco, *Genes Dev.*, 10:3018-3027, 1996.
Murakami et al., *Mol. Gen. Genet.*, 205:42-50, 1986.
Murashige and Skoog, *Physiol. Plant.*, 15:473-497, 1962.
Nagatani et al., *Biotech. Tech.*, 11 (7):471-473, 1997.
Negruk et al., *Plant J.*, 9:137-145, 1996.
Netzer and Hartl, *Nature*, 388:343-349, 1997.
Nixon et al, *Trends Biotechnol.*, 16:258-264, 1998.
Novillo et al., *Proc. Natl. Acad. Sci. USA*, 101:3985-3990, 2004.
Odell et al., *Nature*, 313:810-812, 1985.
Ogawa et al., *Sci. Rep.*, 13:42-48, 1973.
Okamuro et al., *Proc. Natl. Acad. Sci. USA*, 94:7076-7081, 1997.
Omirulleh et al., *Plant Mol. Biol.*, 21(3):415-428, 1993.
Onate-Sanchez and Singh, *Plant Physiol.*, 128, 1313-1322, 2002.
Ow et al., *Science*, 234:856-859, 1986.
Paiva et al., *Plant Mol. Biol.* 17, 653-667, 1991.
PCT App. WO 9217598
PCT App. WO 94/09699
PCT App. WO 95/06128
PCT App. WO 97/4103
PCT App. WO 97/41228
Pompon et al., *Methods Enzymol.*, 272:51-64, 1996.

Post-Beittenmiller, *Annu. Rev. Plant Physiol. Plant Mol. Biol.*, 47, 405-430, 1996.
Potrykus et al., *Mol. Gen. Genet.*, 199:183-188, 1985.
Prasher et al., *Biochem. Biophys. Res. Commun.*, 126(3): 1259-1268, 1985.
Pruitt et al., *Proc. Natl. Acad. Sci. USA*, 97:1311-1316, 2000.
Ptashne, and Gann, In: *Genes and signals*, Cold Spring Harbor: Cold Spring Harbor Laboratory Press, 2002.
Quackenbush et al., *Nucl. Acids. Res.*, 28, 141-145, 2000.
Rawson and Clarke, *Aust. J. Plant Physiol.*, 15, 397-406, 1988.
Reddy et al., *Proc. Natl. Acad. Sci. USA* 102, 16573-16578, 2005.
Reichel et al, *Proc. Natl. Acad. Sci. USA*, 93 (12) p. 5888-5893. 1996.
Restrepo et al., *Plant Cell*, 2:987-998, 1990.
Rhodes et al., *Methods Mol. Biol.*, 55:121-131, 1995.
Riechmann et al., *Science*, 290, 2105-2110, 2000.
Ritala et al., *Plant Mol. Biol.*, 24(2):317-325, 1994.
Ro et al., *Plant Physiol.*, 126:317-329, 2001.
Rogers et al., *Methods Enzymol.*, 153:253-277, 1987.
Sakuma et al., *Biochem. Biophys. Res. Comm.*, 290:998-1009, 2002.
Sambrook et al., In: *Molecular Cloning-A Laboratory Manual* (second edition), Cold Spring Harbour Laboratory Press, 1989.
Sawada et al., *Plant J.*, 31:555-564, 2002.
Schoch et al., *J. Biol. Chem.* 276, 36566-36574, 2001.
Schultz and Haughn, *Plant Cell*, 3:771-781, 1991.
Sheen et al., *Plant Journal*, 8(5):777-784, 1995.
Shimada et al., *Plant Physiol*, 131:941-951, 2003.
Shimokoriyama, *J. Am. Chem. Soc.*, 79:4199-4202, 1957.
Shinozaki et al., *Curr. Opin. Plant Biol.*, 6:410-417, 2003.
Singsit et al., *Transgenic Res.*, 6(2):169-176, 1997.
Skerra, *Curr. Opin. Chem. Biol.*, 7:683-693, 2003.
Spencer et al., *Plant Molecular Biology*, 18:201-210, 1992.
Stalker et al., *Science*, 242:419-422, 1988.
Steele et al., *Arch. Biochem. Biophys.*, 367:146-150, 1999.
Stockinger et al., *Proc. Natl. Acad. Sci. USA*, 94:1035-1040, 1997.
St-Pierre et al., *Plant J.*, 14:703-713, 1998.
Sullivan et al., *Mol. Gen. Genet.*, 215(3):431-440, 1989.
Sutcliffe, *Proc. Natl. Acad. Sci. USA*, 75:3737-3741, 1978.
Tacke et al., *Plant J.*, 8:907-917, 1995.
Tattersall et al., *Science*, 293:1826-1828, 2001.
Thelen and Ohlrogge, *Metab. Eng.*, 4:12-21, 2002.
Thillet et al., *J. Biol. Chem.*, 263:12500-12508, 1988.
Thomas et al., *Plant Sci.* 69:189-198, 1990.
Thomashow, *Annu. Rev. Plant Physiol. Plant Mol. Biol.*, 50, 571-599, 1999.
Thompson et al., *EMBO J.*, 6(9):2519-2523, 1987.
Thompson et al., *Euphytica*, 85(1-3):75-80, 1995.
Thompson et al., *Nucl. Acids. Res.*, 22:4673-4680, 1994.
Tian and Dixon, *Planta* 224:496-507, 2006.
Tian et al., *Plant Cell Rep.*, 16:267-271, 1997.
Tingay et al., *Plant J.*, 11(6): 1369-1376. 1997.
Todd et al., *Plant J.*, 17:119-130, 1999.
Tomes et al., *Plant. Mol. Biol.* 14(2):261-268, 1990.
Torbet et al., *Crop Science*, 38(1):226-231, 1998. Torbet et al., *Plant Cell Reports*, 14(10):635-640, 1995.
Toriyama et al., *TheorAppl. Genet.*, 73:16, 1986.
Tsuchiya et al., *J. Bacteriol.*, 171:3187-3191, 1989.
Tsukada et al., *Plant Cell Physiol.*, 30(4)599-604, 1989.
Uchimiya et al., *Mol. Gen. Genet.*, 204:204, 1986.
Van Eck et al., *Plant Cell Reports*, 14(5):299-304, 1995.
Vasil et al., *Plant Physiol.*, 91:1575-1579, 1989.
Verpoorte and Memelink, *Curr. Opin. Biotechnol.*, 13:181-187, 2002.
Vogg et al., *J. Exp. Bot.*, 149, 2004.
Vogt and Jones, *Trends Plant Sci.*, 5:380-386, 2000.
Walker et al., *Proc. Natl. Acad. Sci. USA*, 84:6624-6628, 1987.
Wang et al., *Molecular Cell. Biol.*, 12(8):3399-3406, 1992.
Wei et al., *Plant Physiol. Biochem.*, 39, 841-848, 2001.
Wellesen et al., *Proc. Natl. Acad. Sci. USA*, 98:9694-9699, 2001.
Werck-Reichhart et al., In *The Arabidopsis Book*, Somerville and Meyerowitz (Eds.), Rockville: American Society of Plant Biologists, 2002.
Williams et al., *Mol. Cell*, 5:121-131, 2000.
Winkel-Shirley, *Plant Physiol.*, 126:485-493, 2001.
Wu et al., *Nat. Biotechnol.*, 23:1013-1017, 2005.
Xia et al., *Plant Cell*, 8, 1291-1304, 1996.
Xia et al., *Plant Physiol.*, 115,925-937, 1997.
Xie et al., *Science*, 299:396-399, 2003.
Xu et al., *Plant Physiol.*, 115,501-510, 1997.
Yamada et al., *Plant Cell Rep.*, 4:85, 1986.
Yang and Russell, *Proc. Natl. Acad. Sci. USA*, 87:4144-4148, 1990.
Ye et al., *Science*, 287:303-305, 2000.
Yu et al., *Plant Physiol.*, 124:781-793, 2000.
Zhang, *Curr. Opin. Plant Biol.*, 6, 430-440, 2003.
Zheng and Edwards, *J. Gen. Virol.*, 71:1865-1868, 1990.
Zhou et al., *Plant Cell Reports*, 12(11). 612-616, 1993.
Zukowsky et al., *Proc. Natl. Acad. Sci. USA*, 80:1101-1105, 1983.

What is claimed is:

1. A DNA construct comprising a promoter functional in a plant operably linked to a nucleic acid sequence encoding a fusion polypeptide comprising a first enzyme and a second enzyme, wherein the first enzyme is a membrane-bound enzyme and the second enzyme is a soluble enzyme, wherein a product of the first enzyme is a substrate of the second enzyme or wherein a product of the second enzyme is a substrate of the first enzyme, wherein the fusion polypeptide comprises the enzymatic activity of the first and second enzymes, and wherein the first and second biosynthetic enzymes are isoflavone synthase and chalcone isomerase.

2. The construct of claim 1, wherein isoflavone synthase is located proximate to the N-terminus of the fusion polypeptide relative to chalcone isomerase.

3. The construct of claim 1, wherein at least one of the first and second biosynthetic enzymes is from a legume.

4. The construct of claim 3, wherein the isoflavone synthase is from soybean.

5. The construct of claim 3, wherein the chalcone isomerase is from alfalfa.

6. The construct of claim 1, wherein the first biosynthetic enzyme is fused to the second biosynthetic enzyme via a peptide linker.

7. A recombinant vector comprising the DNA construct of claim 1.

8. The recombinant vector of claim 7, further comprising at least one additional sequence chosen from the group consisting of: a regulatory sequence, a selectable marker, a leader sequence and a terminator.

9. The recombinant vector of claim 8, wherein the additional sequence is a heterologous sequence.

10. The recombinant vector of claim 8, wherein the promoter is a plant developmentally-regulated, organelle-specific, inducible, tissue-specific, constitutive, cell-specific, seed specific, or germination-specific promoter.

11. A plant cell transformed with the construct of claim 1.

12. A plant transformed with the construct of claim 1.

13. The plant of claim 12, further defined as a monocotyledonous plant.

14. The plant of claim 12, further defined as a dicotyledonous plant.

15. A plant part of the plant of claim 12.

16. A seed of the plant of claim 12, wherein the seed comprises said construct.

17. A method of modifying the isoflavone biosynthesis of a plant, comprising introducing into the plant the construct of claim 1.

18. The method of claim 17, wherein introducing the coding sequence comprises plant breeding.

19. The method of claim 17, wherein introducing the coding sequence comprises genetic transformation.

20. The method of claim 17, wherein genistein and/or daidzein are increased in the plant relative to a plant of the same genotype as said plant that lacks the construct.

21. The method of claim 20, wherein genistein is increased in the plant.

22. The method of claim 20, wherein daidzein is increased in the plant.

23. The method of claim 21, wherein genistein is increased by at least 15% relative to said plant that lacks the construct.

* * * * *